United States Patent [19]
Laughon et al.

[11] Patent Number: 6,046,165
[45] Date of Patent: Apr. 4, 2000

[54] COMPOSITIONS AND METHODS FOR IDENTIFYING AND TESTING TGF-β PATHWAY AGONISTS AND ANTAGONISTS

[75] Inventors: Allen Laughon; Kirby Johnson; Jaeseob Kim, all of Madison, Wis.

[73] Assignee: Ophidian Pharmaceuticals, Inc., Madison, Wis.

[21] Appl. No.: 08/880,729

[22] Filed: Jun. 23, 1997

[51] Int. Cl.$^7$ .......................... A61K 37/00; A61K 31/70; A01N 43/04; C07K 14/00

[52] U.S. Cl. ................................ 514/12; 514/44; 530/350

[58] Field of Search .......................... 530/350; 536/24.1; 574/12, 44

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,556,752 | 9/1996 | Lockhart et al. | 435/6 |
| 5,652,096 | 7/1997 | Cimino | 435/6 |

OTHER PUBLICATIONS

J. Massague,"TGFβSignaling: Receptors, Transducers, and Mad Proteins," *Cell* 85:947–950 (1996).

Attisano et al., "Activation of the signaling by the activin receptor complex." *Mol. Cell. Biol.* 16:, 1066–1073 (1996).

V. Wiersdorff et al., "Mad acts downstream Of Dpp receptors, revealing a differential requirement for dpp signaling in initiation and propagation of morphogenesis in the Drosophila Eye," *Development* 122:2153–2162 (1996).

R. Weiser et al., "GS domain mutations that constitutively activate TGFβR–1, the downstream signaling component in the TGF–β receptor complex," *EMBO J.*, 14:2199–2208 (1995).

F. Liu et al., "A Human Mad Protein Acting As a BMP––regulated Transcriptional Activator," *Nature* 381:620–623 (1996).

R. Derynck and Y. Zhang, "Intracellular Signalling: The Mad Way To Do It," *Curr. Biol.* 6:1226–1229 (1996).

Raftery et al., "Genetic Screens to Identify Elements of the *decapentaplegic* Signaling Pathway In Drosophila," *Genetics* 139:241–254 (1995).

Savage et al., "*Caenorhabditis elegans* genes sma–2, sma–3 and sma–4 define a conserved family of transforming growth factor β Pathway Components," *Proc. Natl. Acad. Sci . USA* 93:790–794 (1996).

Lagna et al., "Partnertship between DPC4 and SMAD proteins in TGF–β singnaling pathways," *Nature* 383:832–836 (1996);

Hoodless et al., "MADRI, a MAD–Related Protein That Functions In BMP2 Signaling Pathways," *Cell* 85:489–500 (1996).

Baker and Harland, "A novel mesoderm inducer, Madr2, functions in the activin signal transduction pathway," *Genes Dev.* 10:1880–1889 (1996).

Vrana et al.,"Expression of Tissue Factor in Tumor Stroma Correlates with Progression to invasive Human Breast Cancer: Paracrine Regulation by Carcinoma Cell–derived Members of the Transforming Growth Factor β Family," *Cancer Res.* 56(21):5063–5070 (1996).

Mercier et al., "Calcitriol and Lexicalcitol (KH1060) Inhibit the Growth of Human Breast Adenocarcinoma Cells by Enhancing Transforming Growth Factor–β Production," *Biochem. Pharmacol.* 52(3):505–510 (1996).

Dannecker et al., "Induction of TGF–beta by an antiprogestin in the human breast cancer cell line T–47D," *Ann. of Onco.* 7(4):391–395 (1996).

Kong, "Elevated Plasma Transforming Growth Factor–$β_1$ Levels in Breast Cancer Patients Decrease After Surgical Removal of the Tumor,"*Ann. Surg.* 222(2):155–162 (1995).

Robson et al., "Transforming growth factor β1 expression in human colorectal tumours: an independent prognostic marker in a subgroup of poor prognosis patients," *Brit. J. Cancer.* 74(5):753–758 (1996).

Tsushima et al., "High Levels of Transforming Growth Factor β1 in Patients With Colorectal Cancer: Assocation With Disease Progression," *Gastroenterol.* 110(2):375–382 (1996).

Akiyama "Transforming Growth Factor β Type II Receptor Gene Mutations in Adenomas From Hereditary Nonpolyposis Colorectal Cancer," *Gastroenterol.* 112(1):33–39 (1997).

Souza et al., "A Transforming Growth Factor β1 Receptor Type II Mutation in Ulcerative Colitis–Associated Neoplasms," *Gastroenterol.* 112(1):40–45 (1997).

Togo et al,, "A Transforming Growth Factor β Type II Receptor Gene Mutation Common in Sporadic Cecum Cancer with Microsatellite Instability," *Cancer Res.* 56(24):5620–5623 (1996).

Fakhrai et al., "Eradication of established intracranial rat gliomas by transforming growth factor β antisense gene therapy," *Proc. of the Natl. Acad. of Sci. USA* 93(7):2909–2914 (1996).

Weller and Fontana, "The failure of current immunotherapy for malignant glioma. Tumor–derived TGF–β, T–cell apoptosis, and the immune privilege of the brain," *Brain Res. Rev.* 21(2):128–151 (1995).

Perry et al., "Transforming Growth Factors Beta as a Clinical Biomarker for Prostate Cancer," *Urology* 49(1):151–155 (1997).

(List continued on next page.)

*Primary Examiner*—Karen Cochrane Carlson
*Attorney, Agent, or Firm*—Medlen & Carroll, LLP

[57] ABSTRACT

The invention provides compositions and methods of identifying and testing TGF-β pathway agonists and antagonists, and in particular compositions comprising Mothers against DPP (MAD) proteins and related Smad polypeptides which exhibit sequence-specific DNA-binding activity. The invention also provides a novel DNA sequence (SEQ ID NO:19); (SEQ ID NO:20); (SEQ ID NO:21) that is bound with high affinity by Drosophila MAD protein. This protein is useful for identifying compounds that will enhance or interfere with MAD protein-DNA binding.

1 Claim, 17 Drawing Sheets

OTHER PUBLICATIONS

Roberson et al., "Fenretinide: Induction of Apoptosis and Endogenous Transforming Growth Factor β in PC–3 Prostate Cancer Cells," *Cell. Growth and Diff.* 8(1):101–111 (1997).

Junker et al., "Transforming Growth Factors Beta 1 is Significantly Elevated in Plasma of Patients Suffering from Renal Cell Carcinoma," *Cytokine* 8(10):794–798 (1996).

M. R. Keeton et al.. "Identification of the regulatory sequences in the type 1 Plasinogen Activator Inhibitor Gene Rresponsive to Transforming Growth Factor β," *J. Biol. Chem.* 34: 23048–23052.

Wrana et al., "TGF–β signals through a heterotrimeric protein kinase receptor complex," *Cell* 71: 1003–1014 (1992).

R. P. deGroot and W. Kruijer, "Transcriptional activation by TGFβ1 mediated by the dyad symmetry element (DSE) and the TPA responsive element (TRE)," *Biochem. Biophys. Res. Commun.* 168:1074–1081(1990).

Chen et al., "A transcriptional partner for MAD proteins in TGF–β signalling," *Nature* 383:691–695 (1996).

Li et al., "Transforming Growth Factor βActivates the promoter of Cyclin–dependent kinase inhibitor p15$^{INK4B}$ through an Sp1 consensus site," *J.Biol.Chem.* 270:26750–26753, (1995).

R. Derynck et al., "Nomenclature: Vertebrate Mediators of TGFβ Family Singnals," *Cell*, 87:173 (1996).

J. Sekelsky et al., "Genetic Characterization And Cloning Of *Mothers Against Dpp*, A Gene Required For *Decapentaplegic* Function In *Drosophila Melanogaster*," *Genetics* 139:1347–1358 (1995).

Marmur and Lane, "Strand Separation and Specific Recombination in Deoxyribonucleic Acids: Biological Studies," *Proc. Natl. Acad. Sci. USA* 46:453–461 (1960).

Doty et al., "Strand Separation and Specific Recombination in Deoxyribonucleic Acids: Physical Chemical Studies," *Proc. Natl. Acad. Sci. USA* 46:461–476 (1960).

Wallace et al.,"Application of Synthetic Oligonucleotides to the Diagnosis of Human Genetic Diseases," *Biochimie* 67:755–762 (1985).

Studencki and Wallace," Allele–Specific Hybridization Using Oligonucleotidee Probes of Very High Specific Acitvity: Discriminaation of the Human β$^A$–and β$^A$–Globin Genes," *DNA* 3: 7–15 (1984).

Studencki et al., "Discrimination Among the Human β$^A$, β$^S$, and β$^C$ –Globin Genes Using Allele–Specific Oligonucleotide Hydridiza tionProbes," *Human Genetics* 37:42–51 (1995).

Smith and Waterman,"Comprison of Biosequences," *Adv. Appl. Math.* 2: 482–489 (1981).

Needleman and Wunsch, "A General Method Applicable too the Search for Similarities in the Amino Acid Sequence of Two Proteins," *J. Mol. Biol.* 48:443–453 (1970).

Pearson and Lipman, "Improved Tools for Biolgical Sequence Comparison," *Proc. Natl. Acad. Sci. (U.S.A.)*85: 2444–2448 (1988).

Y. Zhang edt al., "Receptor–associated Mad Homologues Synergize As Effectors Of The TGF–beta Response," *Nature* 383:168–172 (1996).

Bowie et al., "A Method to Identify Protein Sequences The Fold in to a Known Three–Dimensional Structure," *Science* 253:164–170 (1991).

Thorton et al., "Prediction of progress at last," *Nature* 354:105–106 (1991).

Fauchere, J., "Elements for the Rational Design of Peptide Drugs," *Adv. Drug. Res.* 15:29–67 (1986).

Veber and Freidinger, "The design of metabolically–stable peptide analogs," *TINS* p.392–396 (1985).

Evans et al., "Design of Nonpeptidal Ligands for a Peptide Receptor: Cholecystokinin Antagonists," *J. Med. Chem* 30:1229–1239 (1987).

Rizo & Gierasch, "Constrained Peptides: Models of Bioactive Peptides and Protein Substructures," *Ann. Rev. Biochem.* 61:387–418 (1992).

Cui et al., "TGFβ1 Inhibits the Formation of Bening Skin Tumors, but Enhances Progression to Invasive Spindle Carcinomas in Ttansgenic Mice," *Cell* 86:531–542 (1996).

Border and Ruoshlahti, "Transforming Growth Factor–β in Disease: The Dark Side of Tissue Repair," *J. Clin. Invest.*, 90:1–7 (1992).

Wahl, "Transforming Growth Factor–Beta (TGF–β) in Inflmmation: A Cause and a Cure," *J. Clin. Immunol.* 12(2):61–74 (1992).

Kuhn and Schwenk, Advances in gene targeting methods, *Current Opin. Immunol.* 9: 183–188.

Massague and Weis–Garcia, "Serine/threonine Kkinase Receptors: Mediators of Transforming Growth Factor Beta family Signals," *Cancer Surveys* 27:41–64 (1996).

Sinha et al., "Polymer support oligonucleotide synthesis XVIII: use of β–cyanoethy1–N, N–dialklamino–/N–morpholino phosphoramidite of deoxynucleosides for the synthesis of DNA fragments simplifying deprotection and isolation of the final product," *Nucleic Acids Res.* 12:4539–4567 (1984).

Kadonaga and Tijan,"Affinity purification of sequence–specific DNA binding proteins," *Proc. Natl. Acad. Sci.* (U.S.A.) 83:5889–5893 (1986).

LeTilly & Royer, "Fluorenscence Anisotropy Assays Implicate Protein–Protein Interactions in Regulating trp Repressor DNA Binding," *Biochem.* 32:7753–7758 (1993).

Linn and Riggs, "lac Repressor binding to Non–operator DNA: Detailed Studies and a Comparison of Eqilibrium and Rate Competition Methods," *J. Mol. Bio* 72:671–690 (1972).

Fried and Crothers, "Equilibria and kinetics of lac repressor–operator interactions by polyacrylamide gel electrophoresis," *Nucleic Acids Res.* 9(23):6506–6524 (1981).

Riggs et al., "lac Repressor–Operator Interaction," *J. Mol. Bio.*; 48:67–83 (1970).

Garner and Revzin, "A gel electrophoresis method for quantifying the binding of proteins to specific DNA regions: application to components of the *Echerichia coli* lactose operon regulatory system," *Nucleic Acids Res.* 9:3047–3060 (1981).

Wang and Reed, "Molecular cloning of the olfactory neuronal transcription factor Olf–1 by genetic selection in yeast," *Nature* 364: 121–126 (1993).

Alexandre et al., "Study Heterologous Transcription Factors in Yeast," *Methods* 5: 147–155 (1993).

Luo et al., "Cloning and analysis of DNA–binding proteins by yeast one–hybrid systems," *Biotechniques*, 20: 564–8 (1996).

Fields and O. Strong, "A novel genetic system to detect protein–protein interactions," *Nature* 340:245–246 (1989).

D. J. Lockhart et al., "Expression monitoring by hybridisation to high–density oligonucleotide arrays," *Nat. Biotech.* 14:1675–1680 (1996).

Mcpharron et al., "Regulation of skeletal muscle mass in mice by a new TGF–β superfamily member," *Nature*, 387: 83–90 (1997).

Gould et al., "Targets of homeotic gene control in Drosophila ," *Nature* 348: 308–312 (1990).

Xu and Rubin, "Analysis of Genetic mosaics in developing and adult Drosophila tissues," *Development*, 117:1223–1237 (1993).

Williams et al., "Pattern formation in a secondary field: a hierarchy of regulatory genes subdivides the developing Drosophila wing disc into discrete subregions," *Development* 117:571–584 (1993).

Nelson & A. Laughon, "Drosophila glial architecture and development: analysis using a collection of new cell–specific markers," *Roux Arch. dev. Biol.* 202:341–354 (1993).

Rubin and Spralding, "Genetic Transformation of Drosophila with Transposable Elements Vectors," *Science* 218:348–353 (1982).

S. Blair, "Compartment And Appendage Development In Drosophila, " *BioEssays* 17(4):229–309 (1995).

K. Basler and G. Struhl, "Compartment Boundaries And The Control of Drosophila Limb Pattern by Hedgehog Protein," *Nature* 368:208–214 (1994).

T. Tabata and T. Kornberg, "Hedgehog Is A Signaling Protein With A Key Role In Patterning Drosophila Imaginal Discs," *Cell* 76:89–102 (1994).

Zecca et al., "Sequential Organizing Activities of Engrailed, Hedgehog and Decapentaplegic in the Drosophila Wing," *Development* 121:2265–2278 (1995).

W. Ingram and M.J. Fietz "Quantitative Effects of Hedgehog and Decapentaplegic Activity on the Patterning of the Drosophila Wing," *Curr. Biol.* 5:432–440 (1995).

L. Posakony et al., "Wing Formation In *Drosophila Melanogaster* requires decapentaplegic gene function along the anterior–posterior compartment boundary," *Mech. Dev.* 33:69–82 (1991).

Capdevilla, J. & Guerrero, I., "Targeted expression of the signalling molecule decapentaplegic induces pattern duplications and growth alterations in Drosophila wings," *EMBO J.* 13, 4459–4468 (1994).

Nellen, D. et al. "Direct and Long–Range Action of A Dpp Morphogen Gradient," *Cell* 85, 357–368 (1996).

Lecuit, T. et al., "Two distinct mechanisms for long–range patterning by Decapentaplegic in the Drosophila wing," *Nature* 381:387–393 (1996).

Kim., J. et al, "Integration of positional signals and regulation of wing formation and identity by Drosophila vestigial gene," *Nature* 382:133–138 (1996).

de Celis, J. Fet et al., "A gene complex acting downstream of dpp in Drosophila wing morphogenesis," *Nature* 381, 421–424 (1996).

Grimm, S. and Pflugfleder, G. O., "Control of the Gene optomotor–blind in Drosophila Wing Development by decapentaplegic and wingless," *Science,* 271, 1601–1604 (1996).

K. Eppert et al., "MADR2 Maps to 18q21 and Encode a TGF beta–regualted MAD–related Protein That is Functionally Mutated in Colorectal Carcinoma," *Cell* 86:543–552 (1996).

Chouinard, S. & Kaufman, T. C., "Control of expression of the homeotic labial ( lab ) locus of *Drosophila melanogaster:* evidence for both positive and negative autogenous regulation," *Development* 13: 1267–1280 (1991).

Tremml, G. & Bienz, M., "Induction of *labial* expression in the Drosophia endoderm: response elements for dpp signalling and for autoregulation," *Development* 116:447–456 (1992).

Thuringer, F., et al, "Dissection of an indirect autoregulatory response of a homeotic Drosophila gene," *EMBO J.* 12:2419–2430 (1993).

Chen et al., "A transcriptional partner for MAD proteins in TGF–β signalling," *Nature* 383:691–696 (1996).

Y. Zhang et al., "Tumor Suppressor Smad4/DPC4 as a Central Mediator of Smad Function," *Current Biology* 7:270–276 (1977).

M. Kretzschmar et al., "The TGF–β Family Mediator Smad1 is Phosphorylated Directly and Acitvated Funcitonally by the BMP Receptor Kinase" *Genes & Development* 11:984–995 (1997).

Mastick et al., "Identification of Targets Genes Regulated by Homeotic Proteins in *Drosophila melanogaster* Through Genetic Selection of Ultrabithorax Protein–Binding Sites in Yeast," *Genetics* 139:349–363 (1995).

D.A. Cox, "Transforming Growth Factor–Beta 3," *Cell Biology International* 19:357–371 (1997).

J. Rusch and M. Levine, "Regulation of a dpp target gene in the Drosophila embryo", *Development* 124:303–311 (1997).

Kim S–J et al., "Characterization of the promoter region of the human transforming growth factor–β1 gene," *J. Biol. Chem.* 264(1):402–408 (1989).

Macias–Silva et al., "MADR2 is a substrate of the TGF–β receptor and its phosphorylation is required for nuclear accumulation and signaling" *Cell* 87:1215–1224 (1996).

Graba, Y. et al., "Hometic control in Drosophila; the scabrous gene is an in vivo target of Ultrabithorax ( Ubx ) proteins", EMBO J. 11(9):3375–3384 (1992).

Graff, J.M. et al., "Xenopus Mad proteins transduce distinct subsets of signals for the TGF–β superfamily", *Cell* 85:479–487 (1996).

Liu et al. Jun. 13, 1996. Nature 381: 620–623.

Ayer et al. 1993. Cell 72: 211–222

Sekelsky et al. 1995 Genetics 139: 1347–1358

| | | Relative Affinity |
|---|---|---|
| lab-A | tacgggctGCCGtgGggggagac | 1 |
| Ubx-A | gcctGaCGcCagtccagaaac | 2 |
| lab-C | gagtGCCGcCGttcgatacgattc | 24 |
| Ubx-B | ggaagcGCCGgCGctgacgcc | 100 |
| vg | gcttggctGCCGtCGcgattc | 100 |

GCCGnCGc

FIG. 3C

```
              TRE B
         _____
TRE    CATATGAGTCAGACACCTCTGGCTGTCTGGAAGGGCAT
       _____
        TRE A                 *   *     *   *
          *   *   *

PAI-A  CAACCCTCAGCCAGACAAGGTTGTTGACACAAGAGAGCC
         *   *   *                      *    *

PAI-B  CAAGAGAGCCCCTCAGGGCACAGAGAGAGTCTGGACAC
                  *              *    *   *   *

PAI-C  GAGTCTGGACACGTGGGGGGTCAGCCCGTGTATCATCGG
                                  *   *   *   *
                                             Mix.2 B
                                          _____
          *
         Mix.2 A
       _____
MIX.2  TATCTGCTGCCCTAAAAATGTGTATTCCATGGAAAATGTCTGCCCTTCTCTCC
             *    *    *                               *   *   *   *   * p15    ACAGGGGCGGAGCCTAA
        _____
           Sp1 site
            *   *   *
              *
```

FIG. 5

MAD PREFERS A SYMMETRIC BINDING SITE

CTTGGCTGCCCGTCGCGATTC

↕

CTTGCCGCCCGTCGCGATTC
6X higher
affinity for
Mad

FIG. 7B

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:1:

TGGCTGCCGT CGCGATTC                                            18

(2) INFORMATION FOR SEQ ID NO:2:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

TACGGGCTGC CGTGGGGAGA CACCAGAGCT GTGTAGCAAG AATCGTATCG AACGGCGGCA      60

CTC                                                                                                     63

(2) INFORMATION FOR SEQ ID NO:3:

(i) SEQUENCE CHARACTERISTICS:
        (A) LENGTH: 68 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:3:

GTTTCTGGAC TGGCGTCAGC GCCGGCGCTT CCAGCTGCCA AATTGCTGCT TTATTAGCTG      60

-continued

```
CGTAAGTG                                                             68

(2) INFORMATION FOR SEQ ID NO:4:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:4:

TACGGGCTGC CGTGGGGGGA GAC                                            23

(2) INFORMATION FOR SEQ ID NO:5:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:5:

GCCTGACGCC AGTCCAGAAA C                                              21

(2) INFORMATION FOR SEQ ID NO:6:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:6:

GAGTGCCGCC GTTCGATACG ATTC                                           24

(2) INFORMATION FOR SEQ ID NO:7:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:7:

GGAAGCGCCG GCGCTGACGC C                                              21

(2) INFORMATION FOR SEQ ID NO:8:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"
```

(xi) SEQUENCE DESCRIPTION: SEQ ID NO:8:

GCTTGGCTGC CGTCGCGATT C                                              21

(2) INFORMATION FOR SEQ ID NO:9:

(i) SEQUENCE CHARACTERISTICS:
           (A) LENGTH: 8 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:9:

GCCGNCGC                                                              8

(2) INFORMATION FOR SEQ ID NO:10:

(i) SEQUENCE CHARACTERISTICS:
           (A) LENGTH: 38 base pairs
           (B) TYPE: nucleic acid
           (C) STRANDEDNESS: double
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:10:

CATATGAGTC AGACACCTCT GGCTGTCTGG AAGGGCAT                              38

(2) INFORMATION FOR SEQ ID NO:11:

(i) SEQUENCE CHARACTERISTICS:
           (A) LENGTH: 38 base pairs
           (B) TYPE: nucleic acid
           (C) STRANDEDNESS: double
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:11:

CAACCTCAGC CAGACAAGGT TGTTGACACA AGAGAGCC                              38

(2) INFORMATION FOR SEQ ID NO:12:

(i) SEQUENCE CHARACTERISTICS:
           (A) LENGTH: 38 base pairs
           (B) TYPE: nucleic acid
           (C) STRANDEDNESS: double
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:12:

CAAGAGAGCC CTCAGGGGCA CAGAGAGAGT CTGGACAC                              38

(2) INFORMATION FOR SEQ ID NO:13:

(i) SEQUENCE CHARACTERISTICS:
           (A) LENGTH: 38 base pairs
           (B) TYPE: nucleic acid
           (C) STRANDEDNESS: double
           (D) TOPOLOGY: linear (ii) MOLECULE TYPE: other nucleic acid
           (A) DESCRIPTION: /desc = "DNA"

(xi) SEQUENCE DESCRIPTION: SEQ ID NO:13:

GAGTCTGGAC ACGTGGGGGG TCAGCCGTGT ATCATCGG                               38

(2) INFORMATION FOR SEQ ID NO:14:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

TATCTGCTGC CCTAAAATGT GTATTCCATG GAAATGTCTG CCCTTCTCTC C                 51

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

ACAGGGGGCG GAGCCTAA                                                     18

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

CTTGGCTGCC GTCGCGATTC                                                   20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

CTTGCGCGCC GTCGCGATTC                                                   20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "DNA"

(xi) SEQUENCE DESCRIPTION: SEQ ID NO:18:

TGGAAATGTC TGCCCTTCTC T                                              21

(2) INFORMATION FOR SEQ ID NO:19:

(i) SEQUENCE CHARACTERISTICS:
        (A) LENGTH: 4 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

GCGC                                                                  4

(2) INFORMATION FOR SEQ ID NO:20:

(i) SEQUENCE CHARACTERISTICS:
        (A) LENGTH: 4 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

ACGG                                                                  4

(2) INFORMATION FOR SEQ ID NO:21:

(i) SEQUENCE CHARACTERISTICS:
        (A) LENGTH: 5 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:21:

TCGCG                                                                 5

(2) INFORMATION FOR SEQ ID NO:22:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:22:

TTTGTGCTTG GCTGCCGTCG CGATTCGACA ACTTTGG                              37

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO:23:

TTTGTGCTTG AGATCTAGAT CTATTCGACA ACTTTGG                    37

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:24:

TTTCTGGACT GGCGTCAGGC CGGCGCTTCC AGCTGCCAAA T               41

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:25:

AGCTGCCAAA TTGCTGCTTT ATTAGCTGCG TAAGTGGCTC                 40

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:26:

CTTGGCTGCC GTCGCGATTC                                       20

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:27:

TACGGGCTGC CGTGGGGAGA CACCA                                 25

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: double
        (D) TOPOLOGY: linear

```
        (ii) MOLECULE TYPE: other nucleic acid
            (A) DESCRIPTION: /desc = "DNA"

(xi) SEQUENCE DESCRIPTION: SEQ ID NO:28:

CCAGAGCTGT GTAGCAAGAA                                                    20

(2) INFORMATION FOR SEQ ID NO:29:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:29:

GAATCGTATC GAACGGCGGC ACTC                                               24

(2) INFORMATION FOR SEQ ID NO:30:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:30:

CCGGCGCTTC CAGCTGCCAA AT                                                 22

(2) INFORMATION FOR SEQ ID NO:31:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:31:

CAGCTATGAC CATGATTACG CCAAGC                                             26

(2) INFORMATION FOR SEQ ID NO:32:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:32:

CCAAAGTTGT CGAATAGATC TGGCAGCCAA GCACAAA                                 37

(2) INFORMATION FOR SEQ ID NO:33:

(i) SEQUENCE CHARACTERISTICS:
            (A) LENGTH: 37 base pairs
            (B) TYPE: nucleic acid
            (C) STRANDEDNESS: single
```

```
            (D) TOPOLOGY: linear (ii) MOLECULE TYPE: other nucleic acid
         (A) DESCRIPTION: /desc = "DNA"

(xi) SEQUENCE DESCRIPTION: SEQ ID NO:33:

TTTGTGCTTG AGATCTGTCG CGATTCGACA ACTTTGG                          37

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:34:

GCGTAATACG ACTCACTATA GGGCGA                                      26
```

COMPOSITIONS AND METHODS FOR IDENTIFYING AND TESTING TGF-β PATHWAY AGONISTS AND ANTAGONISTS

FIELD OF THE INVENTION

The invention generally relates to compositions and methods of identifying and testing Transforming growth factor-β (TGF-β) pathway agonists and antagonists, and in particular, compositions comprising Mothers against DPP (MAD) proteins which exhibit sequence-specific DNA-binding activity.

BACKGROUND OF THE INVENTION

The TGF-β superfamily is one of the largest groups of polypeptide growth and differentiation factors. A variety of structural and functional criteria have been used to group the superfamily into three classes: (1) TGF-βs; (2) activins; (3) bone morphogenetic proteins (BMPs). Members of these groups mediate a wide range of biological processes in vertebrates and invertebrates, includings regulation of cell proliferation, differentiation, recognition, and death, and thus play a major role in developmental processes, tissue recycling, and repair (J. Wrana and L. Attisano, "Mad-related Proteins in TGF-β Signaling," TIG 12:493–496, 1996).

Genetic and biochemical studies indicate that TGF-β and related factors, including activin, BMPs and their Drosophila counterpart, Decapentaplegic (DPP) signal to their target cells by simultaneously contacting two transmembrane receptor serine/threonine kinases, known as the type I and type II receptors (J. Massague, "TGFβ Signaling: Receptors, Transducers, and Mad Proteins," Cell 85:947–950, 1996). Receptor activation occurs upon binding of ligand to the type II receptor, which then recruits and phosphorylates the type 1 receptor in its glycine and serine-rich domain. Once phosphorylated, receptor I is activated and then propogates the signal to downstream targets (L. Atisano et al., "Activation of the signaling by the activin receptor complex." Mol. Cell. Biol. 16:, 1066–1073). Also, constitutively active type I receptors (L. Atisano et al., "Activation of the signalling by the activin receptor complex." Mol. Cell. Biol. 16: 1066–1073; V. Wiersdorff et al., "Mad Acts Downstream Of Dpp Receptors, Revealing A Differential Requirement For Dpp Signaling In Initiation and Propagation Of Morphogenesis in the Drosophila Eye," Development 122:2153–2162, 1996), appear to signal biological responses in the absence of ligand and receptor II (RII) (R. Weiser et al, "GS domain mutations that constitutively activate TGFβ R1, the downstream signaling component in the TGFβ receptor complex," EMBO J., 14:2199–2208), which indicates the role of the type I receptor (RI) as the downstream or the essential transducing element.

Although, the molecular workings of the TGF-β receptors are reasonably well understood, little is known of the downstream intermediate targets that transmits the Ser/Thr kinase receptor signals from the cell membrane to the nucleus. Recent studies indicate that signaling by TGF-β-like molecules may be transduced by a set of evolutionary conserved proteins known as Smads, which upon activation directly translocate to the nucleus, where they may activate transcription (F. Liu et al., "A Human Mad Protein Acting As A BMP-regulated Transcriptional Activator," Nature 381:622–623, 1996). Five Smad proteins, designated Smad 1–5, have been so far characterized in vertebrates (R. Derynck and Y. Zhang, "Intracellular Signalling: The Mad Way To Do It," Curr. Biol. 6:1226–1229, 1996). These factors are related to the intracellular mediators of DPP signaling, mothers against dpp (MAD) in the fruitfly Drosophila melanogaster (L. Raftery et al., "Genetic Screens to identify elements of the Decapentaplegic Pathway In Drosophila," Genetics 139:241–254 (1995)., and to the Sma genes from the nematode Caenorhabditis elegans (C. Savage et al., "C. Elegans Genes Sma-2, Sma-3 and Sma-4 Genes Define A Conserved Family Of TGF-β Pathway Components," Proc. Natl. Acad. Sci. USA 93:790–794, 1996; R. Derynck and Y. Zhang, "Intracellular Signalling: The Mad Way To Do It," Curr. Biol. 6:1226–1229, 1996). Signaling causes Smads to form hetero-oligomers. BMP signaling stimulates Smad1 to form a complex with Smad4; activin signaling stimulates Smad2 to form a complex with Smad4 (G. Lagna et al., "Partnership Between DPC4 and Smad Proteins in TGF-β Signaling Pathways," Nature 383:832–836, 1996). It is speculated that common responses to multiple ligands might be mediated by overlap in the regulation of some Smad proteins, while localized expression and activation of specific Smads may mediate specific biological responses (J. Wrana and L. Attisano, "MAD-related Proteins in TGF-β Signalling," TIG 12:493–496, 1996).

There is little information at present as to how these Smads and homologous proteins might elicit cellular responses. Analysis of Smad1 suggests that this protein resides predominantly in the cytoplasm in unstimulated cells, but accumulates in the nucleus upon activation of BMP signaling pathways (P. A. Hoodless et al., "MADR1, A MAD-related Protein That Functions In BMP2 Signaling Pathways," Cell 85:489–500, 1996). Similarly, the nuclear localization of a lacZ-Smad2 fusion protein, expressed in Xenopus ectoderm explants, is enhanced by the addition of activin (J. C.Baker & R.Harland, Genes Dev. 10:1880–1889, 1996). Also, a lacZ fusion with a C-terminal fragment of Smad2 displays constitutive nuclear localization, suggesting that the N-terminal domain can act to retain Smad proteins in the cytoplasm (J. C.Baker & R.Harland, Genes Dev. 10:1880–1889, 1996). Although the nature of the signals that control Smad protein localization is not clear, the function of these intracellular proteins is to transmit signals from the cytoplasm to the nucleus resulting in the activation of target gene expression.

Regardless of the precise nature of the pathway, there is evidence that TGF-β plays a role in the pathogenesis of impaired wound healing, human fibrotic diseases, autoimmune diseases, atherosclerosis and malignancy. Overproduction or under-production of TGF-βs underlie these pathologies. Importantly, manipulation of TGF-β levels has been shown to reverse these pathologies in experimental models of human disease. Increased TGF-β normalizes the wound healing defects in aged or glucocorticoid treated rats. Administration of TGF-β has been shown to ameliorate EAE, a model of multiple sclerosis, and experimental arthritis. Antibodies to TGF-β exacerbate the symptoms in these models.

TGF-β has at least two important roles in cancer. It is growth inhibitory to many cells so that loss of responsiveness to TGF-β through mutation of receptor or Smad proteins results in uncontrolled proliferation. Second, it is highly immunosuppressive so that tumor cells no longer responsive to TGF-β themselves, up-regulate the expression of TGF-β to protect themselves from the immune system. Increased expression of TGF-β may also enhance the ability of the tumor cells to migrate to new sites during metastasis. Breast Cancer: TGF-β mRNA has been quantitated in human breast carcinomas. In a group of 24 samples, over-expression of TGF-β was detected in 75% of the tumors. The increase did not correlate with grade, estrogen responsiveness, progesterone receptor status or lymph node involvement [Christeli et al. (1996) *Oncol. Rpts.* 3(6) :1115–1118].

Tissue factor (TF), the cellular initiator of the protease blood coagulation cascade, is expressed in the stroma of breast tumors progressing to invasive cancer. This expression is induced by conditioned media (CM) from breast cancer cells and the CM effect is blocked by anti-TGF-β antibodies. Tumor cell-derived TGF-β induction of stromal cell TF is an early event in progression to invasive breast cancer [Vrana et al. (1996) *Cancer Res.* 56(21):5063–5070].

The antiproliferative effects of calcitriol and lexicalcitol (KH1060) on human breast epithelial cells has been shown to be blocked by the presence of anti-TGF-β [Mercier et al. (1996) *Biochem. Pharmacol.* 52(3):505–510].

The antiproliferative effects of the antiprogestin onapristone correlated with its ability to increase TGF-β production of human breast cancer cell lines [Dannecker et al. (1996) *Ann. of Onco.* 7(4):391–395].

81% of breast cancer patients had elevated plasma TGF-β levels of more than two standard deviations above the normal mean [Kong (1995) *Ann. Surg.* 222:2].

Colon and Gastric Cancer: Increased TGF-β expression in colorectal tumors has been shown to be correlated with poor prognosis [Robson et al. (1996) *Brit. J. Cancer.* 74(5) :753–758]. In addition, plasma TGF-β levels are higher in patients with colorectal cancer. Levels of mRNA and protein are higher in the tumor tissue [Tsushima et al. (1996) *Gastroenterol.* 110(2):375–382].

Alteration in type II receptor (RII) has been found in 57% of adenomas and 85% of colon tumors in 10 patients studied, indicating a strong association between RII mutations and progression of disease [Akiyama (1997) *Gastroenterol.* 112 (1):33–39]. Evaluation of 138 human tumors for type II receptor mutations concluded that these mutations were associated with a subset of ulcerative colitis carcinomas, common (81%) in sporadic colorectal cancers and rare in gastric and esophageal cancer [Souza et al. (1997) *Gastroenterol.* 112(1):40–45].

In addition, examination of RII mutations in 112 cases of gastrointestinal and hepatobiliary cancer found replication error in 17 tumors and also RII mutations in 10 of those 17 tumors (3 of 4 gastric and 7 of 10 colorectal) [Togo et al. (1996) *Cancer Res.* 56(24):5620–5623].

Glioma: Gliomas express immunosuppressive TGF-β. In a rat model, 9L gliomasarcoma cells were modified to express a TGF-β antisense plasmid. 11 of 11 animals survived for 12 weeks compared to 2 of 15 control animals with 9L cells. In animals treated with TGF-β antisense therapy, there was no evidence of residual tumor. Inhibition of TGF-β expression significantly enhanced tumor-cell immunogenicity [Fakhrai et al. (1996) *Proc. of the Natl. Acad. of Sci. USA* 93(7) :2909–2914]. However, at present, human malignant gliomas are resistant to all current therapeutic approaches.(See review: Weller and Fontana "Malignant glioma cells". *Brain Res. Rev.* 21(2):128–151, 1995).

Lung Cancer: The association of TGF-β has also been made with lung cancer. In one study, elevated TGF-β levels (~3 fold) were detected in the plasma of 50% (27/54) lung cancer patients [Kong et al. ((196) *Lung Cancer* 16(1) :47–59].

Prostate Cancer: Increased levels of urinary TGF-β 1 and plasma TGF-β 2 have also been reported in patients with prostate cancer [Perry et al (1997) *Urology* 49(1):151–155]. Review: [Steiner (1995) *World J. Urol.* 13(6):329–336].

Fenretinide (4-HPR), a retinoid derivative with antineoplastic activity, when used to treat prostate cancer cells (PC-3) caused apoptosis, increased TGF-β 1 mRNA and protein levels and increased TGF-β receptor 1 expression. The cytotoxixity was blocked by addition of anti-TGF-β 1. A resistant breast cell line BT-20 did not show increased TGF-β in response to 4-HPR [Roberson et al. (1997) *Cell. Growth and Diff.* 8(1):101–111].

Renal Cell carcinoma: Levels of latent TGF-β 1 produced in renal cell carcinoma patients has been reported to be approximately 10-fold higher than in healthy controls, which may be responsible for the local immunosuppressive effects seen within the tumor [Junker et al (1996) *Cytokine* 8(10):794–798].

Other Cancers: The above-specified cancers are by no means the only types having an association with TGF-β. They are simply illustrative. These examples make it evident that a better understanding of the role and function of members of the TGF-β cascade is needed in order to circumvent the onset and progression of many types of cancer.

SUMMARY OF THE INVENTION

The invention generally relates to compositions and methods of identifying and testing TGF-β pathway agonists and antagonists, and in particular, compositions comprising Mothers against DPP (MAD) proteins which exhibit sequence-specific DNA-binding activity. In one embodiment, the present invention contemplates a MAD protein whose DNA binding activity is unmasked when its carboxy-terminal domain is removed. This protein is useful for identifying compounds that will enhance or interfere with MAD protein—DNA binding.

It is not intended that the present invention be limited to particular MAD proteins or particular nucleic acid binding sequences. A variety of closely related vertebrate homologues of MAD are contemplated (collectively referred to as Smads) that are involved in the regulation of Smad-DNA binding activity by members of the TGF-β superfamily of growth and differentiation factors, including TGF-β, activins, bone morphogenetic proteins (BMPs) and inhibins, and to cis regulatory DNA sequences that are specifically bound by Smad proteins.

The present invention contemplates complexes of specific DNA sequences and MAD or Smad polypeptides. In one embodiment, the MAD or Smad polypeptide of the complex is not the full-length native polypeptide. Rather, it is a portion of the full-length native polypeptide. Preferably, this portion or fragment contains the DNA binding site. In one embodiment, the portions are part of fusion proteins; in such cases, the fusion protein comprises i) a DNA binding region of a Smad (or MAD) polypeptide and ii) a non-Smad (or non-MAD) portion. In one embodiment, the non-Smad portion is a tag useful for purification of the fusion protein (e.g. MBP or hexa-histidine).

It is not intended that the present invention be limited to the highest affinity binding interactions of MAD or Smad polypeptides and DNA. For example, but not by way of limitation, the present invention contemplates complexes of DNA and Smad (or MAD) wherein the DNA has the wild-type (or native) sequence. In another embodiment, the DNA sequence of the complex contains one or more nucleotide analogs. In yet another embodiment, the complexes of DNA and Smad (or MAD) have DNA that is mutated relative to the wild-type sequence. Relative binding affinities for such mutant sequences are readily calculated (see the Examples, below, where the binding to the wild-type sequence is set at 100%). The present invention contemplates DNA complexes with Smad (or MAD) polypeptides wherein the DNA is a mutant sequence and the affinity of Smad (or MAD) binding is at least 30% of the wild-type sequence, and more preferrably at least 50% of the wild-type sequence. In some embodiments, the sequence variation increases binding of Smad or MAD polypeptides; complexes containing such sequences are also contemplated.

Similarly, the present invention is not limited to the native sequence of MAD or Smad polypeptides. Even where portions or fragments are employed, these portions or fragments may have altered amino acid sequences. Thus, the present invention also contemplates DNA-protein complexes comprising MAD or Smad analogues.

The present invention also contemplates compound screening using a variety of assay formats. In one embodiment, the present invention contemplates a method for compound screening, comprising: a) providing: i) a MAD protein or homologue capable of binding to a specific nucleic acid sequence, ii) a nucleic acid substrate comprising said specific nucleic acid sequence, and iii) one or more compounds for screening; b) mixing, in any order, said MAD protein or homologue, said nucleic acid substrate and said one or more compound and c) measuring the extent of protein binding to said nucleic acid substrate.

In one embodiment of the above-described method, the MAD or Smad polypeptide is labelled. In another embodiment, the nucleic acid is labelled.

DESCRIPTION OF THE FIGURES

FIG. 1 shows the binding of MAD$^N$ protein to the vg quadrant enhancer is sequence-specific.

FIG. 2 shows the N-terminal domain of Mad protein (MAD$^N$) binds to the vg quadrant enhancer. FIG. 2(c) is a photograph of an autoradiogram showing the results of a representative gel mobility shift assay used for assessing the ability of MBP-MAD fusions to bind to a $^{32}$P-end-labeled 20 bp vg double-stranded oligo. Lane 1: no protein control: lane 24: unfused MBP; remaining sets of lanes contain progressive 5-fold increases in the proteins labeled as in panel a.

FIG. 3 shows lab endodermal and Ubx midgut enhancers contain MAD$^N$ binding sites similar to those in the vg quadrant enhancer. FIG. 3(c) shows the alignment of sequences (SEQ ID NO:4); (SEQ ID NO:5); (SEQ ID NO:6); (SEQ ID NO:7); (SEQ ID NO:8) that are bound by MAD$^N$ in panel b. The GCCGnCGc consensus (SEQ ID NO:9) derived from the aligned sequences matches the two highest affinity sites perfectly, contains one mismatch with a moderate affinity site, and contains two-three mismatches with two low affinity sites.

FIG. 5 depicts the DNA sequences (SEQ ID NO:10); (SEQ ID NO:11); (SEQ ID NO:12); (SEQ ID NO:13); (SEQ ID NO:14); (SEQ ID NO:15) of the TGF-β response element oligonucleotides used as probes for gel-shift assays with MBP-Smad proteins. Lines above the sequences indicate the extent of the TRE A, TRE B, Mix.2A and Mix.2B probes. PAI-A, -B, -C: denote overlapping oligonucleotides that span the −740 to −646 TGF-β response element of the human plasminogen activator inhibitor (PAI) gene (M. R. Keeton et al., Identification of the regulatory sequences in the type1 PAI gene resposive to TGF-β," J. Biol. Chem. 34: 23048–23052; J. L. Wrana et al., "TGF-β signals through a heterotrimeric protein kinase receptor complex," Cell 71: 1003–1014, 1992). TRE, the −74 to −42 TPA responsive element of the human collagenase gene (R. P. deGroot and W. Kruijer, "Transcriptional activation by TGF-β 1 mediated by the dyad symmetry element (DSE) and the TPA responsive element (TRE), Biochem. Biophys. Res. Commun. 168:1074–1081; Wrana et al., Cell 71: 1003–1014, 1992). Mix-2: denotes the Activin responsive element of the Xenopus Mix.2 gene (X. Chen et al., "A transcriptional partner for MAD proteins in TGF-β signaling, "Nature 383: 691–695. 1996). p15: denotes the oligonucleotide probe that spans −83 to −66 TGF-β response element of the human p15$^{INK4B}$ gene (J-M. Li et al., "TGF-β activates the promoter of cyclin-dependent kinase inhibitor p15$^{INK4B}$ through an Sp1 consensus site," J.Biol.Chem. 270:26750–26753, 1995). The position of the Sp1 binding site within p15 probe is shown as underline. The GNC triplets are highlighted in red. Circled G's were mutated to A's in TREA$^M$ and TREB$^M$ probes.

FIG. 6(A–D) shows the results of gel shift assays.

FIG. 7B depicts the sequence (SEQ ID NO:16) of the MAD-DNA binding site, and indicates particular nucleotide substitutions, i.e., changing of GCT to CGC (see downward arrow) (SEQ ID NO:17) increases the binding affinity of MAD to its cognate site, 6 fold.

DEFINITIONS

Figure 1A:
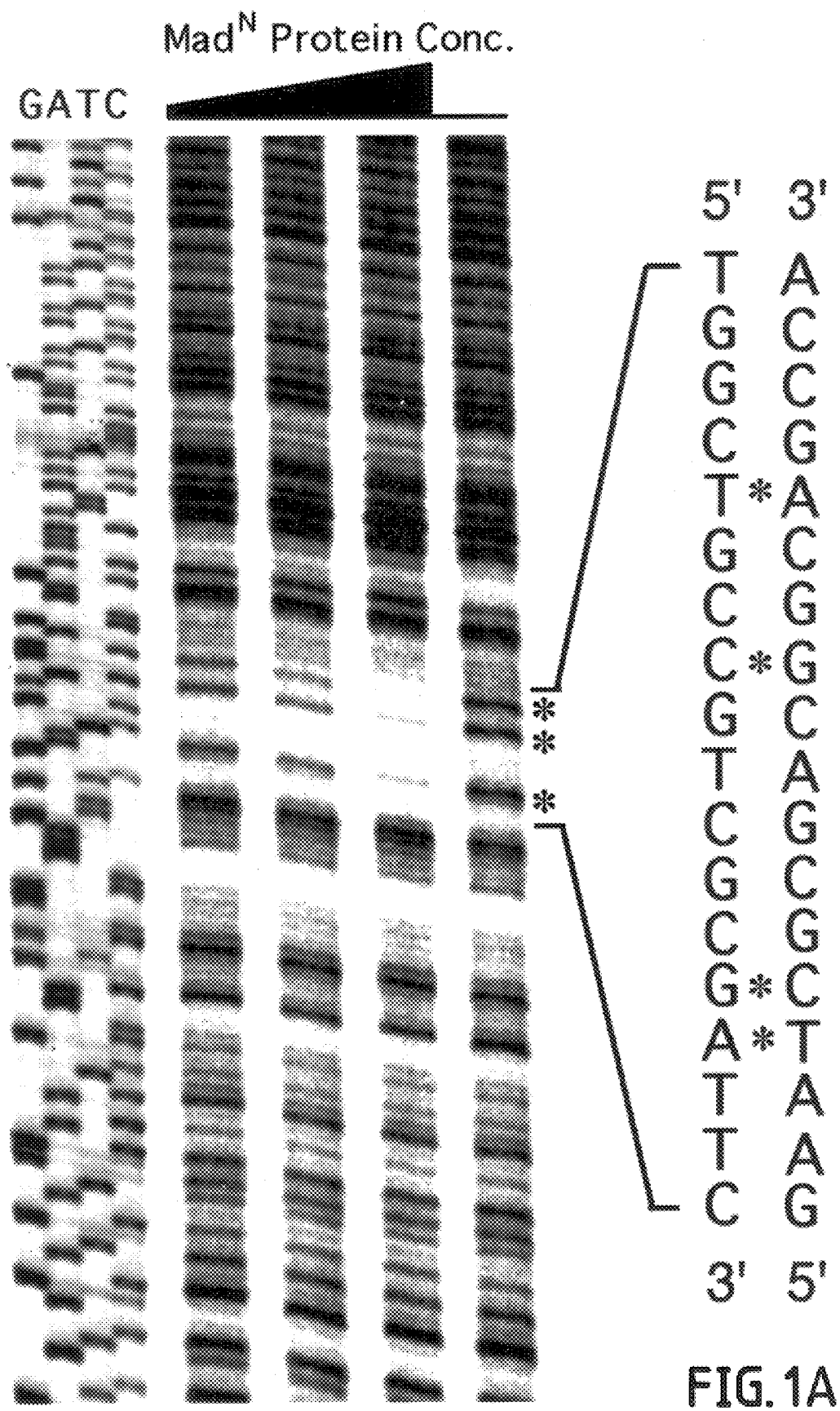
FIG. 1(a) is a photograph of a representative gel showing the DNase I footprint (SEQ ID NO:1) of the MAD$^N$ protein to the vg quadrant enhancer.

To facilitate understanding of the invention, a number of terms are defined below.

There is a generally accepted nomenclature for the vertebrate mediators of the TGF-β family signals (see R. Derynck et al., Cell, 87:173, 1996). The Mad (mothers against decapentaplegic) gene in Drosophila and the related Sma genes in *Caenorhabditis elegans* have been implicated in signal transduction by factors of the TGF-β family (see J. Sekelsky et al., "Genetic Characterization And Cloning Of Mothers Against Dpp, A Gene Required For Decapentaplegic Function In *Drosophila Melanogaster,*" Genetics 139:1347–1358, 1995; Savage et al., "*Caenorhabditis elegans* genes sma-2, sma-3, and sma-4 define a conserved family of transforming growth factor beta pathway components," Proc. Natl. Acad. Sci.(USA), 93:790–794, 1996). Related genes have been identified recently in vertebrates and shown to mediate TGF-β family signals in these organisms as well. Todate, there are five family members described as full length protein sequences in human, mouse, and/or Xenopus. Because of their diversity and simultaneous identification in different laboratories, the MAD-related products in vertebrates have received different names. In order to facilitate future work and the dissemination of information in this area, it has been proposed to unify the nomenclature of the vertebrate genes and their products by referrring to them as "Smad." This term, a merger of Sma and Mad, differentiates these proteins from unrelated gene products previously called Mad. It has been proposed that each individual family member be designated as follows:

Smad1

GeneBank accession numbers are U54826, U57456, U58992, U59423, U58834, and L77888, Smad1 has been previously referred to as Madr1, bsp1, Dwarfin-A, Xmad, Xmad1, and JV4-1.

Smad2

GeneBank accession numbers are U59911, U60530, U65019, U68018 and L77885. Smad2 has been peviously referred to as Madr2, hMAD-2, Xmad2, and JV18-1.

Smad3

Gene Bank accession number is U68019. Smad3 has been previously referred to as hMAD-3.

Smad4

Also referred to in the human as DPC4 (deleted in pancreatic carcinoma). GenBank accession number is U44378. Smad4 has been previously referred to as Xmad4.

Smad5

GenBank accession number is U58993. SmadS has been previously referred to as Dwarfin-C.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., *Biochimie* 67:755 (1985). In the case of radioactive oligonucleotide probes, only extremely high specific activities are found to show satisfactory results. See Studencki and Wallace, *DNA* 3:1 (1984) and Studencki et al., *Human Genetics* 37:42 (1985).

K. B. Mullis et al., U.S. Pat. Nos. 4,683,195 and 4,683,202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers arc extended with a polymerase so as to form a new pair of complementary strands. There can be numerous "cycles" to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction"

(hereinafter PCR). Because the desired amplified segments of the target sequence become the predominant sequences (in terms of concentration) in the mixture, they are said to be "PCR amplified".

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Such labels can be added to the oligonucleotides of the present invention.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. patent application Ser. No. 08/231,440, hereby incorporated by reference.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, viruses, protozoans, fungi, and ciliates.

The term "microbial gene sequences" refers to gene sequences derived from a microorganism, including but not limited to, bacteria.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparision; a reference sequence may be a subset of a larger sequence, for example, as a segment of a full-length MAD cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (USA.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length MAD protein or enhancer cDNA sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., various fragments of Mad protein). Fragments typically are at least 14 amino acids long, preferably at least 20 amino acids long, usually at least 50 amino acids long or longer, and span the portion of the polypeptide required for intermolecular binding of MAD to the specific DNA sequence in the enhancer region.

The term "analog" as used herein refers to polypeptides which are comprised of a segment of at least 25 amino acids that has substantial identity to a portion of the deduced amino acid sequence of MAD. The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antigonists or agonists of MAD function by inclusion in screening assays described herein below.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (c.g.,$^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In anothers, the label is part of the fusion protein. (e.g. GFP).

GENERAL DESCRIPTION OF INVENTION

The invention generally relates to compositions and methods of identifying and testing TGF-β pathway agonists and antagonists, and in particular, compositions comprising Mothers against DPP (MAD) proteins which exhibit sequence-specific DNA-binding activity. MAD proteins activate gene expression in response to an extracellular growth and differentiation factor called decapentaplegic (DPP). MAD and DPP are homologous to vertebrate proteins that function in TGF-β signaling pathways. Biological processes that are affected by these pathways include inhibition of cell proliferation and tumor progression, formation and patterning of cartilage and bone, healing of fractures, suppression of immune reactions, formation and patterning of the central nervous system and eye, tooth development, kidney development, lung development, gut development, skin and hair development, inhibition of pituitary FSH, genital duct regression, oogenesis and spermatogenesis.

A preferred MAD protein of the present invention contains a sequence-specific DNA-binding activity within its conserved N-terminal domain 1. While a precise understanding of the mechanisms involved is not necessary to the practice of the screening methods of the present invention, it is believed that a) domain 1 also mediates oligomerization of MAD that is necessary for binding to DNA and b) phosphorylation of MAD in response to extracellular DPP activates DNA binding by disrupting the interaction between domain 1 and domain 2, resulting in the activation of transcription from specific target genes.

The invention also identifies a DNA sequences that bind to MAD and Smad polypeptides, including a novel DNA sequence (SEQ ID NO:19); (SEQ ID NO:20); (SEQ ID NO:21), GCGC/ACGG/TCGCG, that is bound with high affinity by MAD and shows that these are essential features of a cis regulatory element that activates transcription in response to extracellular DPP.

It is not intended that the present invention be limited to particular MAD proteins or particular nucleic acid binding sequences. A variety of closely related vertebrate homologues of MAD are contemplated (collectively referred to as Smads that are involved in the regulation of Smad-DNA binding activity by members of the TGF-β superfamily of growth and differentiation factors, including TGF-β, activins, bone morphogenetic proteins (BMPs) and inhibins, and to cis regulatory DNA sequences that are specifically bound by Smad proteins.

Production of MAD and related Polypeptides

The nucleotide and amino acid sequences of mammalian MAD protein (e.g., human, murine) are available from GenBank (#U10328; PIR: S55019; Swiss Protein: P42003 and are published (Y. Chang et al., "Receptor-associated Mad Homologues Synergize As Effectors Of The TGF-beta Response," Nature 383:168–172,1996; F. Liu et al., "A Human Mad Protein Acting As A BMP-regulated Transcriptional Activator," Nature 381:622–623, 1996), incorporated herein by reference) thereby enabling those of skill in the art to produce polypeptides corresponding to all or part of the full-length polypeptide sequences. Such polypeptides may be produced in prokaryotic or eukaryotic host cells by expression of polynucleotides encoding MAD, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y. and Berger and Kimmel, Methods in Enzymology, Volume 152, Guide to Molecular Cloning Techniques (1987), Academic Press, Inc., San Diego, Calif.

Fragments or analogs of MAD polypeptides may be prepared by those of skill in the art. Preferred amino- and carboxy-termini of fragments or analogs occur near boundaries of functional domains. For example, but not for limitation, such functional domains include domains conferring the property of binding to form a Smad-DNA or MAD-DNA binding complex.

One method by which structural and functional domains may be identified is by comparison of the nucleotide and/or amino acid sequence data to public or proprietary sequence databases. Preferably, computerized comparison methods are used to identify sequence motifs or predicted protein conformation domains that occur in other proteins of known structure and/or function, such as the zinc fingers. (Proteins, Structures and Molecular Principles, (1984) Creighton (ed.), W. H. Freeman and Company, New York, which is incorporated herein by reference). Further, a method to identify protein sequences that fold into a known three-dimensional structure are known (Bowie et al. (1991) Science 253: 164). Thus, the foregoing examples demonstrate that those of skill in the art can recognize sequence motifs and structural conformations that may be used to define structural and functional domains in the MAD sequence.

Fragments or analogs comprising substantially one or more functional domain may be fused to heterologous polypeptide sequences, wherein the resultant fusion protein exhibits the functional property(ies) conferred by the fragment. Alternatively, polypeptides wherein one or more functional domain have been deleted will exhibit a loss of the property normally conferred by the missing fragment.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of MAD or Smad polypeptides can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to a native MAD or Smad protein. However, analogs must comprise a segment of 25 amino acids that has substantial identity to a portion of the native protein amino acid sequence. Preferred amino acid substitutions are those which: (1) reduce susceptibility to proteolysis, (2) reduce susceptibility to oxidation, (3) alter binding affinity for Smad-DNA or MAD-DNA binding, and (4) confer or modify other physicochemical or functional properties of such analogs. Analogs include various mutants of a Smad or MAD sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts.

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles, 1984) Creighton (ed.), W. H. Freeman and Company, New York; Introduction to Protein Structure, (1991), C. Branden and J. Tooze, Garland Publishing, New York, N.Y.; and Thornton et al. (1991) Nature 354: 105; which are incorporated herein by reference).

It may be advantageous to employ a peptide analog of the MAD or Smad protein, or a portion thereof, as a pharmaceutical agent or as a commercial research reagent. For example, a peptide analog of MAD having high affinity for binding DNA may be used as a competitive inhibitor of complex formation by competing with native MAD for binding to DNA. In addition to polypeptides consisting only of naturally-occuring amino acids, peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human Smad, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH) CH$_2$—, and —CH$_2$SO—, by methods known in the art. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., are not contact points in MAD-protein complexes) to which the peptidomimetic binds to produce the therapeutic effect. Derivitization (e.g., labelling) of peptidomimetics should not substantially interfere with the desired biological or pharmacological activity of the peptidomimetic. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

Additional preferred embodiments comprise MAD and Smad polypeptide analogs that have superior stabilities as experimental reagents. For example, preferred analogs may be resistant to degradation by proteolytic activities present in the binding reaction(s), and/or may be resistant to oxidative inactivation. Such analogs may include amino acid substitutions which remove proteolytic cleavage sites and/or replace residues responsible for oxidative inactivation (e.g., methionine, cysteine). However, the analogs must be functional in at least the control binding assay(s); therefore, analogs comprising amino acid substitutions which destroy or significantly degrade the functional utility of the analog in the binding assay are not employed for such assays.

Uses Of The Present Invention

The invention will be useful for, among other things, (1) the design and execution of screens to identify proteins or small molecules that interact with Smads to activate or prevent activation of DNA binding, and thereby activate or prevent activation of genes that are regulated by TGF-β signaling pathways; (2) screens to identify and clone genes that are directly regulated by TGF-β signaling pathways; (3) the use of specific DNA sequences to identify new MAD or Smad family members; (4) methods for rational drug design; and (5) the development of gene therapy protocols involving the use of Smad-DNA binding activity to treat cancer, autoimmune and hereditary diseases.

(1–2) Screening Assays

The screening assays of the present invention may utilize isolated or purified forms of the assay components (MAD-DNA binding sites or Smad polypeptide[s]). "Purified" refers to polypeptides of the present invention which have been separated from their native environment (e.g., a cytoplasmic or nuclear fraction of a cell, yeast protoplasm, or by recombinant production), preferrably to at least about 10–50% purity. A substantially pure composition includes such polypeptide(s) or complexes that are approaching homogeneity, i.e., about 80–90% pure, preferably 95–99% pure. Preferred embodiments include binding assays which use MAD and Smad polypeptides which are produced by recombinant methods or chemically synthesized. The methods of screening may involve labeling MAD and related polypeptides with any of a myriad of suitable markers, including radiolabels, various fluorescent labels and enzymes, (e.g., glutathione-S-transferase, luciferase, and beta-galactosidase).

It is contemplated that the screening assays of the present invention will, among other things identify agents that will inhibit the TGF-β pathway. Such inhibitors are contemplated to be useful in the treatment of cancer (e.g. counteracting the immunosuppression generated by the TGF-β produced by the tumors and allowing the immune system to eliminate the tumor), fibrosis (e.g. by preventing the excess ECM production in lung disease, kidney disease, myelofibrosis in the bone marrow, and scarring of skin wounds), hematopoiesis (e.g. inhibition of endogenous TGF-β's inhibitory effects on hematopoeitic precursors might have a synergistic effect with agents that promote hematopoiesis), diabetes, heart disease (e.g. by interfering with the effects of increased TGF-β associated with restenosis The screening assays (items 1 and 2, above) are described in more detail in the Detailed Description of Preferred Embodiments. The remaining uses (itens 3, 4 and 5) are described in general terms here.

(3) Identification of New MAD or Smad Family Members

The present invention contemplates using specific sequences for the identification of new MAD or Smad polypeptides. In one embodiment, the present invention contemplates identifying these new polypeptides using DNA affinity chromatography.

DNA affinity chromatography for purification of sequence-specific DNA-binding proteins was originally developed with multimerized synthetic oligonuclcotides covalently coupled to agarose resins. Since then, a variety of other DNA affinity resins have also been developed.

It is not intended that the present invention be limited by the nature of the resin used. In one embodiment, the resin (e.g. sepharose, latex) is in the form of beads. Beads have several advantages for purification of sequence-specific DNA-binding proteins. First, beads are able to immobilize relatively large amounts of DNA. Second, DNAs coupled on the beads are more accessible to DNA-binding proteins because the beads are free to move in the binding mixture. Third, the property of the bead with a hydrophilic surface lowers nonspecific proteins binding on it. Fourth, the batch-wise purification procedure reduces the contamination of nonspecific proteins because the volume of the beads precipitated after a brief centrifugation is extremely small.

These advantages enable one to directly purify sequence-specific DNA-binding proteins from crude cell extracts within a few hours. This particular method has been successfully employed in the purification of several transcription factors.

(4–5) Gene Therapy and Drug Design

Currently, the targets and assays for measuring the activity of TGF-β signaling pathways within cells are few and give limited information. The discovery of MAD and Smad DNA binding activity and the DNA sequence specificity of this binding provides a more sensitive assay that can be used to quantitate the activity of TGF-β signaling pathways in whole tissues or individual cells. The Smad-DNA binding assay provides the means for the development of screens to identify pathway agonists or antagonists and pathway regulated genes as potential therapeutics and diagnostic or prognostic tools for diverse types of cancers, autoimmune diseases and hereditary diseases.

In this regard, TGF-beta signaling has been implicated as a factor contributing to certain cancers [Cui et al., Cell 86:531 (1996)] to fibrosis in disease and wound healing [Border and Ruoshlahti, J. Clin Invest. 90:1 (1992)], and to immune suppression and autoimmune diseases [S. M. Wahl, J. Clin. Immunol. 12:61 (1992)]. The vast differences among these diseases suggests that the various detrimental effects of TGF-beta signaling may result from different subsets of target genes. The ability to identify functional DNA binding sites for MAD and Smad proteins provides the basis for drug or gene therapies that target specific DNA sites, thereby modulating activation or repression of specific genes in response to TGF-beta signaling. The present invention contemplates utilizing human genome information on structure of functional Smad binding sites to perform computer based genome-wide scans for potential Smad response elements. A subset of these sequences will reside near genes that are activated or repressed in response to TGF-beta signaling. In diseases where elevated TGF-beta signaling plays a role, such Smad binding sites are potential targets for the development of drugs or gene therapy protocols.

With regard to drugs, in one embodiment, the present invention contemplates drugs capable of intercalating with DNA-MAD or DNA-Smad binding sites. Polymides have been shown to be capable of sequence-specific binding to the minor groove of DNA, thereby inactivating a specific promoter, while leaving other genes unaffected, both in vitro and in vivo. Methylation interference experiments have shown that Smad proteins contact DNA in the major groove (KJ and AL, unpublished), however it is not known whether there is also minor groove contact that could be disrupted by an appropriately designed polyamide.

With regard to gene therapy, it is contemplated that gene targeting resulting in the mutation, deletion or replacement [Kuhn and Schwenk, Current Opin. Imunnol. 9:183 (1997)] of particular MAD or Smad target DNA binding sites can be used to treat certain diseases. For example, TGF-beta secretion by gliomas appears to suppress immune tumor surveillance, possibly by preventing lymphocyte activation or survival [Fakhara et al., Proc. Nat. Acad. Sci. USA 93:2909 (19960; Weller and Fontana, Brain Res. Rev. 21:128 (1995)]. By inactivating the TGF-beta response elements of key target genes that mediate suppression of T cells, it may be possible to restore the ability of these cells to proliferate and to recognize, infiltrate and destroy gliomas. Susceptible T cells are growth arrested by TGF-beta (Wahl, 1992), possibly by activation of p15 or repression of c-myc [Massague and Weis-Garcia, Cancer Surveys 27:41 (1996)]. TGF-beta immune suppression may also be mediated in part by expression of an inhibitor of the IL-1 receptor and repression of IL-2 receptor expression.

Although most human hereditary diseases result from mutations that alter protein structure, there are examples where the mutational defect lies outside the protein coding region and thus apparently exerts its effect by altering gene expression. It is contemplated that mutation of certain functional DNA binding sites for Smad proteins results in altered gene expression that causes disease, or predisposition to disease. Such mutations may be inherited, or arise in somatic cells. The ability to identify functional Smad binding sites, provides the basis for understanding the underlying mechanism of any such disease or predisposition to disease. In addition, the ability to identify functional MAD or Smad binding sites, and to recognize mutational disruption of such sites also provides the basis for diagnosis of any such disease or predisposition to disease by means of standard PCR-based techniques for determining genotype at a specific genetic locus. Furthermore, the ability to identify functional MAD or Smad binding sites, and to recognize mutational disruption of such sites also provides the basis for developing therapies for the prevention or treatment of any such disease. This includes gene therapy to repair mutant DNA sites (Kuhn and Schwenk, 1997) and drugs that inhibit, activate or bypass any steps in a TGF-beta signaling pathway in such a way as to reverse, block or in some other way alleviate the detrimental effects of a Smad binding site mutation.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.) which is incorporated herein by reference) which are provided throughout this document. All the information contained therein is incorporated herein by reference.

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

Assays for detecting the ability of agents to inhibit or enhance MAD-DNA binding provide for facile high-throughput screening of agent banks (e.g., compound libraries, peptide libraries, and the like) to identify antagonists or agonists. Such TGF-β pathway antagonists and agonists may be further developed as potential therapeutics and diagnostic or prognostic tools for diverse types of cancers, autoimmune diseases and hereditary diseases.

1. Screens to Identify Agonists or Antagonists of Smad-DNA Interaction

There are several different approaches contemplated by the present invention to look for small molecules that specifically inhibit or activate the interaction of a given DNA-binding protein with its binding sequence (cognate site). One approach is to test biological or chemical compounds for their ability to preferentially block the binding of one specific DNA:protein interaction but not others. Such an assay would depend on the development of at least two, preferably three, DNA:protein interaction systems in order to establish controls for distinguishing between general DNA-binding molecules (polycations like heparin or intercalating agents like ethidium) and DNA-binding molecules having sequence binding preferences that would affect protein/cognate binding site interactions in the preferred system but not the other(s).

A. In vitro assays

Molecules selected for testing/screening are added to a test system composed of (a) the Smad protein, and (b) the Smad-DNA cognate binding site (double-stranded oligonucleotide). Selected molecules are incubated in the test system for a period sufficient to permit binding of the molecule being tested to the Smad-DNA complex. The amount of Smad protein bound to the duplex DNA is compared before and after adding a test molecule. Comparison of the amount of Smad protein bound to the duplex DNA before and after adding a test molecule can be accomplished using various read-out systems which measure various protein-DNA interactions, both qualitatively and quantitatively. For example, using microtitre binding assays, filter-binding assays or gel band-shift assays.

a. Solid Phase Binding Assays

In vitro solid phase binding assays utilize methods that measure binding of MAD or Smad proteins to DNA, to identify compounds that promote or disrupt such binding. If desired for basic binding assays, the target polypeptide (MAD or Smad) may be immobilized by standard techniques. For example, but not by way of limitation, such immobilization may be effected by linkage to a solid support, such as a chromatographic matrix, or by binding to a charged surface, such as a Nylon 66 membrane. Binding assays generally take one of two forms: immobilized DNA binding sites can be used to bind MAD or related Smad polypeptide(s), or conversely, immobilized MAD or Smad polypeptide(s) can be used to bind DNA binding sites. In each case, the labeled component is contacted with the immobilized component under aqueous conditions that permit specific binding of the polypeptides(s) to form a MAD- or Smad-DNA complex in the absence of added agent. Particular aqueous conditions may be selected by the practitioner according to conventional methods. For general guidance, the following buffered aqueous conditions may be used: 10–250 mM NaCl, 5–50 mM Tris HCl, pH5–8, with optional addition of divalent cation(s) and/or metal chelators and/or nonionic detergents and/or membrane fractions. It is appreciated by those skilled in the art that additions, deletions, modifications (such as pH) and substitutions (such as KCl substituting for NaCl or buffer substitution) may be made to these general conditions. Modifications can be made to the binding reaction conditions so long as specific binding of MAD or related Smad polypeptides occurs in the control reaction(s). Conditions that do not permit specific binding in control reactions (no agent included) are not suitable for use in binding assays.

Preferably, the MAD or Smad polypeptide is labeled with a detectable marker. Suitable labeling includes, but is not limited to, radiolabeling by incorporation of a radiolabeled amino acid (e.g., $^{14}C$-labeled leucine, $^{3}H$-labeled glycine, $^{35}S$-labeled methionine), radiolabeling by post-translational radioiodination with $^{125}I$ or $^{131}I$ (e.g., Bolton-Hunter reaction and chloramine T), labeling by post-translational phosphorylation with $^{32}P$ (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the DNA binding site is generally labeled with a detectable marker.

Additionally, in some embodiments, MAD or a Smad polypeptide may be used in combination with an accessory protein (e.g., a protein which forms a complex with the polypeptide in vivo such as another Smad polypeptide). In such a case, it is preferred that different labels are used for each polypeptide species, so that binding of individual and/or heterodimeric and/or multimeric complexes can be distinguished. For example but not by way of limitation, a MAD or Smad polypeptide may be labeled with fluorescein and an accessory polypeptide (another Smad protein) may be labeled with a fluorescent marker that fluorescesces with either a different excitation wavelength or emission wavelength, or both. Alternatively, double-label scintillation counting may be used, wherein a Smad polypeptide is labeled with one isotope (e.g., $^{3}H$) and a second polypeptide species is labeled with a different isotope (e.g., $^{14}C$) that can be distinguished by scintillation counting using discrimination techniques.

Labeled polypeptide(s) are contacted with immobilized cognate DNA binding sites under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of between approximately 1 and 15 seconds, although longer incubation periods are preferable so that, in some embodiments, a binding equilibrium is attained. Binding kinetics and the thermodynamic stability of bound MAD or Smad complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (Proteins, Structures and Molecular Principles, (1984) Creighton (ed.), W. H. Freeman and Company, New York).

In one embodiment, specific binding of labeled MAD or a Smad polypeptide to an immobilized DNA binding site, is determined by including a non-specific unlabeled competitor protein(s) (e.g., albumin). After a binding reaction is completed, labeled polypeptide(s) that is/are specifically bound to immobilized DNA is detected. For example, and not by way of limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding of a MAD or Smad polypeptide in a control binding reaction. Blocking agents are included to inhibit nonspecific binding of labeled protein to an immobilized DNA binding element and/or to inhibit nonspecific binding of labeled polypeptide to the immobilized substrate.

In embodiments where a polypeptide is immobilized, linkage to a substrate may be used. Covalent linkage chemistries include, but are not limited to, well-characterized methods known in the art (Kadonaga and Tijan (1986) *Proc. Natl. Acad. Sci. (USA.)* 83: 5889, which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a MAD or Smad polypeptide to the cognate binding site. Agents that inhibit binding relative to the control reaction(s) are thereby identified as MAD-modulating agents.

In a preferred embodiment, the assay measures binding of a labeled DNA probe to a Smad fragment or full length protein that is immobilized on the plastic surface of a microtitre plate. The DNA probe is a double stranded DNA containing a high affinity Smad binding site, and labeling is by means of either a radioactive or fluorescent tag. The probe is generated by annealing of synthetic oligonucleotides. Probes as short as 17 bp can be used for this purpose. Controls that demonstrate the specificity of this assay include (A) a Smad point mutation (corresponding to MAD R107C) reduces binding affinity for the probe >100-fold, (B) a series of mutations in the DNA probe that reduce probe binding by 10- to 100-fold, (C) a stoichiometric excess of non-labeled wild-type DNA competes with the labeled probe for binding to the Smad protein while excess mutant DNA does not.

In a preferred closely related alternative to the above embodiment, the assay measures binding of Smad protein to DNA that has been immobilized within a microtitre well. DNA is immobilized directly on the plastic, or to a resin such as Sepharose. Bound Smad protein is detected by means of a fluorescently labeled antibody that is specific for the Smad, or for an epitope tag that has been fused to the Smad. This embodiment also enables for the in vitro testing of Smad-Smad interactions or oligomerization which may occur prior to DNA binding and gene transcription.

b. Fluorescent Polarization Assay for DNA Binding:

A second type of in vitro binding assay utilizes fluorescence polarization. Fluorescent polarization assays were based on the increase of the rotational correlation time of a fluorochrome-labeled DNA molecule upon the binding of a protein [LeTilly & Royer, Biochem. 32:7753 (1993)]. The protein-DNA complex, due to its increased size, tumbles more slowly than does free DNA. The ensuing reduction in the rotational correlation time of the fluorophore causes an increase in polarization, which allows the binding to be monitored. As shown in equation 1, polarization is defined as the ratio of the difference between the vertical ($\int_{\parallel}$) and horizontal ($\int_{\perp}$) emission components to their sum.

$$\mathcal{P} = 10^3 m\mathcal{P} = \frac{\int \parallel - \int \perp}{\int \parallel + \int \perp} \quad (1)$$

In a preferred embodiment, neither component of the assay is immobilized on the plate and in vitro binding of MAD or a Smad polypeptide to a fluorescent DNA probe is detected in solution. As explained above, binding of protein to the DNA slows the rate at which the labeled probe tumbles in solution and thereby increases fluorescence polarization, which is measured with a commercially available instrument (Panvera Beacon 2000). Both specific and non-specific DNA substrates can be used in the fluorescent polarization assays: oligonucleotide binding sites as described for gel shift assays (see FIG. 5), and a 25-bp dIdC oligonucleotide is useful for this purpose [(dIdC)25.(dIdC) 25]. A fluorescein tag can be linked to oligonucleotides by a six-carbon spacer to the terminal 5'-OH group of one strand of each duplex. Fluorescein can be incorporated from its phosphoramidite in the final coupling state of DNA synthesis. To increase the fluorescein specific activity, the fluorescein-labeled strands can be purified by chromatography on an immobilized anti-immunofluorescein antibody column. Briefly, the strand is loaded onto the column in 10 mM sodium phosphate buffer (pH 6.0) containing EDTA (0.10 mM) and NaCl (0.10M). The loaded column is washed with the same buffer, and the strand is then eluted by denaturing the antibodies with aqueous HCl (0.2M). The resulting solution is neutralized by addition of KOH (0.2M). The purified strand is annealed to its complement, and the resulting duplex is purified by native gel electrophoresis.

Fluorescence polarization is typically measured at room temperature (25±2° C.) on instruments such as a Beacon Fluorescent Polarization System (PanVera, Madison, Wis.) with excitation at 488 nM and emission at 520 nM. Fluorescein-labeled DNA duplex (450–550 pM) is incubated in a solution (1.10 mL) of 25 mM Bis-Tris/Tris/Bis-Tris propane-HCl buffer (pH 7.5) containing EDTA (2 mM), DTT (1 mM), and the indicated concentration of NaCl (this buffer system is used to allow analyses of pH dependence). In a preferred embodiment, unlabelled competitor DNA is used in the fluorescence polarization assay to increase the specificity of the reaction. Aliquots of MAD or Smad are added successively to the solution, which is then allowed to equilibrate. In each assay, the MAD or Smad polypeptide concentration can vary from 10 pM to 5 $\mu$M but the total volume of the solution typically is varied by less than 10%. Three to six polarization measurements are made at each protein concentration. The dissociation constants are determined by fitting the data with the program SIGMAPLOT 4.16 to equation 2 or 3, which describes binding to specific site and nonspecific sites respectively:

$$B = \frac{B_{max}F}{K_d + F} \quad (2)$$

$$B = \frac{B_{max}F}{K_d + F} + K_{ns}F \quad (3)$$

In the above equations, B is the concentration of bound protein, $B_{max}$ is the total concentration of binding sites, F is the concentration of free protein, and $K_d$ is the dissociation constant for specific binding. $K_{ns}F$ is a constant for nonspecific binding.

Additional assays available for detection of Smad-DNA interaction in vitro on a limited scale include co-immunoprecipitation, DNase I footprinting, and nitrocellulose filter binding (also see Experimental, methodology section, for details). Although, not as readily adapted for high throughput screening as microtiter plate-based assays, these assays are available for initial screening or for use in follow-up studies of lead compounds that emerge from other high throughput screening assays.

c. Filter Binding Assays

Filter Binding provides a simple and sensitive means of characterizing the binding of proteins to a known regulatory sequence, as well as various nonspecific DNAs. It is based on the principle that double-stranded DNA flows through nitrocellulose while protein or protein-DNA complexes are retained. Filter Binding is also a useful procedure for determining the DNA-binding properties of pure proteins with unknown functions. Frequently, (e.g., with developmentally important genes) a gene product that is biologically important is known to reside in the nucleus, but its precise function is obscure. Filter binding can be used to identify DNA sequences that interact with these proteins. This assay is ideal for kinetic and equilibrium studies because bound DNA can be rapidly separated from free DNA.

The use of radioactively labeled double-stranded DNA fragments allows quantitation of DNA bound to the protein at various times and under various conditions, permitting kinetic and equilibrium studies of DNA-binding interactions. Purified protein is mixed with double stranded DNA in an appropriate buffer to allow interaction. After incubation, the mixture is suction filtered through nitrocellulose, allowing unbound DNA to pass through the filter while the protein (and any DNA interacting with it) is retained.

Competition experiments using filter binding allow rigorous determination of the relative affinities that several sequences have for one protein. In addition, kinetic measurements can be performed that allow a good estimate of the binding constant and off-rate for any given protein-DNA interaction.

The $K_{eq}$ of a protein for DNA, can be calculated from filter-binding data obtained by equilibrium or rate competition experiments as described by Lin and Riggs [J. Mol. Bio 72:671 (1972)]. Equilibrium concentration experiments involve the mixing of various amounts of cold competitor with a fixed amount of labeled specific DNA during the binding incubation. The amount of competitor needed to reduce labeled specific DNA retained measures the affinity of the protein for that competitor. Such experiments are particularly useful when the competitor is is a single stranded nucleic acid that could bind directly to the filter, precluding a direct measurement, or when the competitor is difficult to label [Riggs et al., J. Mol. Bio. 48:67 (1970)].

In one embodiment of the present invention, the test molecule to be screened is added to a test reaction comprising: (a) the Smad protein, and (b) the double-stranded DNA oligonucleotide. The molecule is incubated in the test reaction for a period sufficient to permit binding of the compound being tested to the Smad-DNA oligonucleotides complex. Unbound test oligonucleotides are separated from Smad-DNA complex bound to the binding protein by passing the test reaction through a filter, where the filter is capable of capturing DNA:protein complexes but not DNA that is free of protein. The separated test oligonucleotides are then amplified. These amplified test oligonucleotides are then recycled through the screening steps of the assay in order to obtain a desired degree of selection. The amplified test oligonucleotides are isolated and sequenced. The amplification step in the method may be accomplished by polymerase chain reaction or other methods of amplification, including, cloning and subsequent in vivo amplification of the cloning vector containing the sequences of interest.

The filter binding method is also useful in determining the half-life for oligonucleotide:protein complexes, because the separation of DNA:protein complexes from free probe is very rapid.

d. Gel Mobility Shift Assay

Gel mobility Shift assays (abbreviated EMSA or band-shift assay) were based on the retardation of the electrophoretic mobility of a $^{32}$P-labeled DNA molecule upon the binding of a protein [Fried and Crothers, Nucleic Acids Res. 9:6506 (1981); Garner and Revzin, Nucleic Acids Res. 9:3047 (1981)].

Figure 3A:
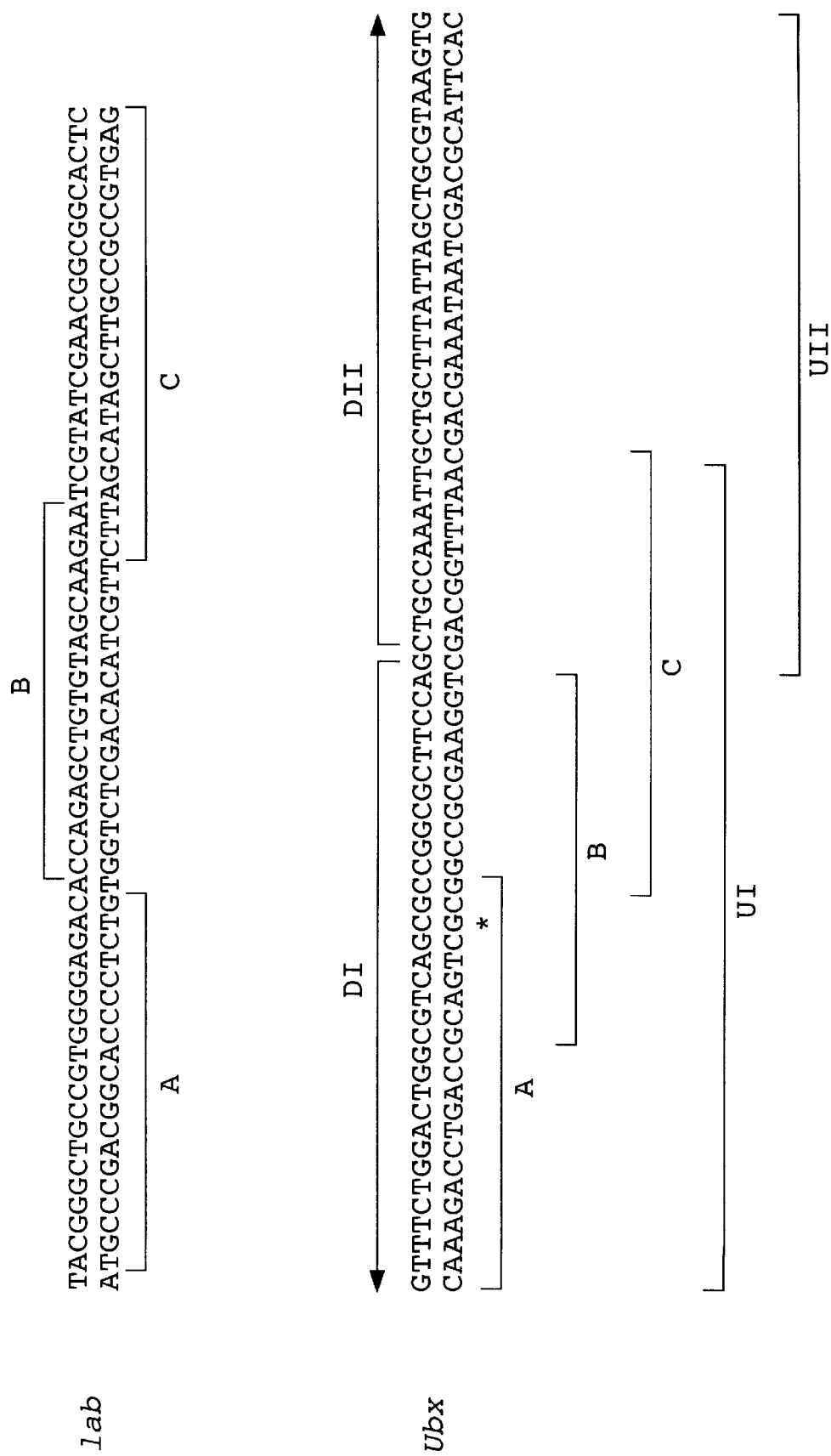
FIG. 3(a) depicts the DNA sequences of a portion of the lab endodermal enhancer (SEQ ID NO:2) and of the DI and DII regions of the Ubx midgut enhancer (SEQ ID NO:3), each of which contains sequences resembling the MAD binding site of the quadrant enhancer. The regions corresponding to the probes used for the gel mobility shift assay in panel b are marked with brackets. Asterisk indicates a base pair that was omitted in the Ubx-A probe.
Figure 3B:
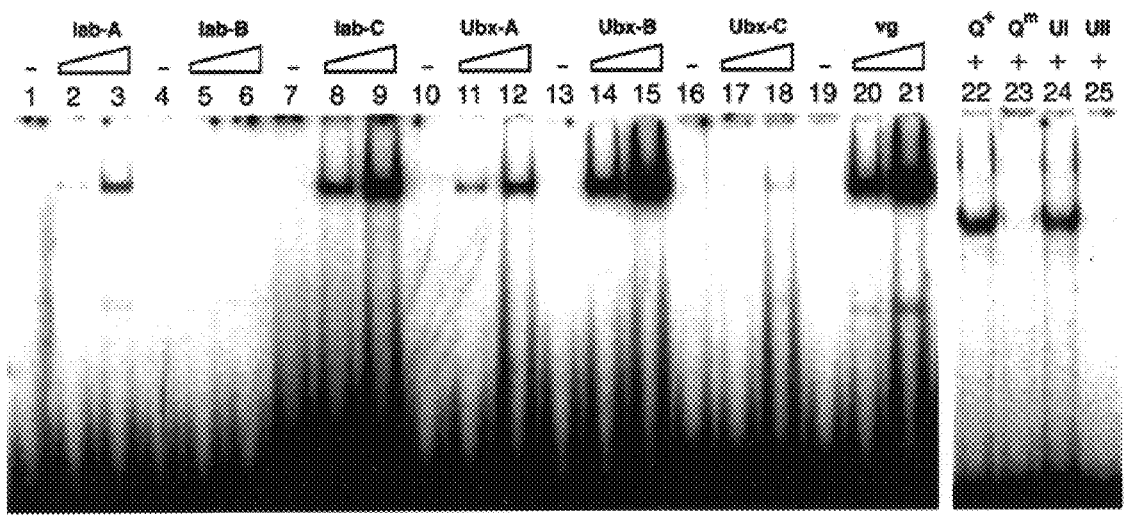
FIG. 3(b) is a photograph of an autoradiogram showing the results of a representative gel mobility shift assay, which identifies a high affinity MAD$^N$ binding site in the lab enhancer and one in the Ubx DI region. The sequences of the lab (SEQ ID NO:2) and Ubx (SEQ ID NO:3) probes are shown in panel a. vg is a 20 bp probe containing the MAD$^N$ binding site while Q$^+$ and Q$^m$ are 40 bp probes containing wild-type and mutated versions of the same site. Each set of 30 μl binding reactions contained, from left to right, 1, 100 and 500 ng of fusion protein, as indicated by the minus sign and wedge.

In a preferred embodiment, affinity purified MAD or Smad proteins are incubated with a TGF-β response element (double-stranded TGF-β response element oligonucleotides used as probes for gel-shift assays with MBP-Smad proteins are shown in FIGS. 3 and 5) probes ($2\times10^4$ cpm per reaction, 5' end labeled with [g-$^{32}$P] ATP [6000 Ci/mmole, NEN] and T4 polynucleotide kinase) in binding buffer (25 mM Tris [pH 7.5], 80 mM NaCl, 35 mM KCl, 5 mM MgCl2, 1 mM DTT, 10% glycerol [v/v], 50 mg/ml poly (dI.dC), 50 mg/ml poly (dA.dT), 150 mg/ml non-specific competitor DNA [random double-stranded oligonucleotides or sonicated salmon sperm DNA]) for 20 min at room temperature. Binding reactions can contain 3.3 mg/ml poly (dI.dC) without other nonspecific competitor DNA. The binding reaction mixtures are subjected to low ionic strength (22.5 mM Tris base, 22.5 mM boric acid) electrophoresis in 5% polyacrylamide gels. Autoradiographic images of dried gels can be generated with a Molecular Dynamics Phosphor Imager and this data used for quantitative analyses of binding affinity. Relative binding affinities are based on bound probe/total probe ratios. The disappearance of the band corresponding to free DNA is followed to determine the equilibrium dissociation constant. The data is conveniently analyzed with the program SIGMAPLOT 4.16 (see Fluorescent Polarization assay for DNA binding, eq. 2, which describes the binding to a single site) (also see Experimental Section, Example 5 for more details).

e. DNase I Footprinting

Another example of a system designed to detect sequence-specific Smad-DNA binding drugs is DNA footprinting. In one embodiment, footprinting can be used to determine the site of protein contact along the ribose-phosphate DNA backbone. A cloned DNA fragment is [$^{32}$P]-labeled at one end, incubated with the MAD or Smad protein of interest and digested lightly with DNaseI such that there is an average of one cut per DNA fragment. The DNA is fractionated by electrophoresis through a denaturing acrylamide gel alongside a sequencing ladder that indicates the position of each band in the resulting DNase I cleavage ladder. Protection from DNase I results in the loss of bands corresponding to the sequence where binding of the protein prevents contact by DNase1. (for protocol and other details, see Experimental, methodology section).

B. In vivo Assays a. Yeast One-hybrid System

A yeast one-hybrid system can be used to identify genes encoding proteins that bind to a target, cis-acting regulatory element or any other short DNA-binding sequence. Detection of the DNA-protein interactions occurs while proteins are in their native configuration, and the gene encoding the DNA-binding protein of interest is available immediately after library screening (M. M.Wang & R. R. Reed, Nature 364: 121–126; C. Alexander et al., Methods 5: 147–155). The yeast one-hybrid assay (commercially available from ClonTech, see I,uo et al, "Cloning & analysis of DNA-binding proteins by yeast one-hybrid and one-two-hybrid systems," Biotechniques, 20: 564–8, 1996) is based on the interaction between a target-specific DNA-binding protein of interest, and a target-independent GAL1 activation domain (see S. Fields & O. Strong, Nature 340: 245). cDNA candidates that may encode the protein of interest are expressed as fusions with the activation domain.

In a preferred embodiment, a yeast one-hybrid system can be used to assay Smad-DNA interaction in vivo. The assay measures activation of a reporter gene in response to Smad binding to a site positioned upstream of a basal promoter. The DNA binding domain of the Smad protein is fused to the transcriptional activation domain (e.g., from the GAL4 protein). The reporter gene encodes a protein that can be detected by histochemical staining (e.g., beta-galactosidase) or by auto-fluorescence (i.e., Green Fluorescent Protein [GFP]). Compounds that pass freely across cell membranes can be tested using the one-hybrid assay for the ability to enhance or disrupt Smad-mediated transcriptional activation. Differences in DNA binding specificity exists between Smad1, Smad2, Smad3 and Smad4, indicating that it will be feasible to create reporters that are specific for individual Smads. Compounds that are specific for Smad-DNA interaction will not affect the activity of a control one-hybrid system employing a different DNA binding domain-DNA binding site combination (i.e., the GAL4 DNA binding domain combined with a UAS Gal binding site-driven reporter). The principle of the yeast one-hybrid system can be adapted for use in other types of cells, including bacteria, and mammalian cultured cells. A bacterial system is inexpensive and easily manipulated, while mammalian cells more closely approximate the in vivo environment in which Smad proteins normally operate.

C. Read-Outs of the Assays

The in vitro and in vivo assays described above will identify compounds that either enhance or antagonize specific binding of MADs or Smads to cognate DNA sites by promoting or disrupting respectively: (A) base-specific surface contact with function groups in the major or minor grove (methylation interference experiments have demonstrated that MAD and Smad4 make multiple base-specific contacts in the major groove), (B) non-sequence-specific contact phosphate backbone contact with DNA, (C) Smad-Smad oligomerization; and (D) other aspects of Smad secondary or tertiary structure that are important for DNA contact.

In addition, these assays are also capable of identifying compounds that act as agonists for DNA binding by full-length MAD protein possibly by certain other full-length Smad proteins. DNA binding is masked by the MH2 domain in full-length MAD. Compounds that disrupt this masking would behave as agonists of the masked DNA binding activity.

D. Secondary Assays

The present invention contemplates a variety of follow-on assays once a candidate agonist or antagonist has been identified. Agonists or antagonists of Smad-DNA binding can be characterized for the specificity of their effects on biological responses known to be affected by signaling pathways downstream of TGF-β superfamily of ligands. This can be done by applying the agonists or antagonists to cells or tissues or whole animals (embryos or adults) in the presence or absence of one of the TGF-β superfamily ligands, including but not limited to TGF-β 1, TGF-β 2, TGF-β 3, activin, inhibin, a bone morphogenetic protein (BMP), Muellerian inhibiting substance or a growth and differentiation factor (GDF).

An agonist might activate one or more of the biological responses in the absence of any of the ligands. An antagonist might inhibit one or more of the biological responses in the presence of any of the ligands.

a. Cells and Cell Lines

For example, cell division in mink lung epithelial cells is inhibited by TGF-β. It is contemplated that an antagonist identified in a Smad-DNA binding assaty can be readily tested for its ability to interfere with the ability of TGF-β to inhibit cell division of mink lung epithelial cells.

Other examples of readily testable systems include fibroblasts. Fibroblast cell lines respond to TGF-β by increasing the expression of extracellular matrix proteins such as fibronectin. The effect of agonists or antagonists on such cell type specific responses to TGF-β can be tested by using different cell lines (in comparison) with known responses. For example, an antagonist could be tested on different cell lines and the results might show that it inhibits the TGF-β induced production of fibronectin in fibroblasts but does not affect the TGF-β induced inhibition of cell proliferation in epithelial cell lines.

It is not intended that the present invention be limited to particular cell lines. The above examples of cell lines are simply by way of illustration and are not the only tests known to those experienced in the art.

i. Differential Display

Importantly, cell lines may be evaluated in their responses by testing for the differential expression of genes. One method for such testing is differential display. Differential display-polymerase chain reaction or DDRT-PCR can be used for the identification of genes that are differentially expressed at the mRNA level. The method is directed toward the identification of differentially expressed genes, detecting individual mRNA species that are changed in different sets of eukaryotic cells, and then permitting recovery and cloning of their DNA.

Differential display provides a picture of the mRNA composition of cells, by displaying subsets of mRNAs as short cDNA bands. This display is useful in the same way as are two-dimensional protein gels, for example, in observing alterations in gene expression. Second, these cDNAs can be quickly sequenced; thereby a sequence unique for each mRNA can readily be obtained and compared with sequences in data banks. Third, individual bands can readily be cloned and then used as probes for northern or Southern blotting and to isolate genes from genomic or cDNA libraries. A comprehensive set of these genes obtained from a display are useful for genetic applications and for preparing antibodies via corresponding amino acid sequences.

Differential display has many advantages over the alternative subtractive hybridization. Only a few micrograms of total RNA is required, compared to 50 fold or more for substractive hybridization. It is much quicker; 2 months are required to isolate clones from cells by subtractive hybridization, but with differential display band patterns are obtained in 2 days and clones in 1 week. There are far fewer technical difficulties with differential display. Most mRNAs should be represented in the pattern as only one band. Redundancy and under representation of rare mRNAs occurring in subtractive hybridization are therefore avoided. Reproducibility and sensitivity are obtained. Multilane displays comparing sets of cells select for both positive and negative differences unique to a process. Most importantly, since the assay can be checked at each step, it is no longer necessary, as with other methods, to wait until the end of the procedure to determine whether it worked properly. These advantages would make this a method of choice for detecting and isolating differentially expressed genes.

The general strategy for differential display is as follows. It depends on a combination of three techniques: (i) reverse transcription from anchored primers; (ii) choice of arbitrary primers for setting lengths of cDNAs to be amplified by the PCR, each corresponding to part of a mRNA (tags); and (iii) sequencing gels for high resolution. The objective is to obtain a tag of a few hundred bases, which is sufficiently long to uniquely identify a mRNA and yet short enough to be separated from others by size. Pairs of primers are selected so that each will amplify DNA from about 100 mRNAs because this number is optimal for display on one lane of the gel.

For the initial reverse transcription one can use a 4-mer that consists of a stretch of 12 Ts plus 2 or more 3' bases, which anchors the primer to the poly(A) tail of many mRNAs. To amplify cDNA tags by PCR one adds a definite, arbitrary 10-mer. Arbitrary primers have been used before to amplify DNA polymorphisms, and more recently to obtain mRNA tags for differentially expressed genes. The majority of mRNAs should be represented if the 12 possible 3' primers and a set of 5' primers are used in all combinations for independent amplifications and displays. Successful applications of the method are emerging using either a limited number of primer combinations or more impressively using 312 combinations of primer pairs made of all 12 possible anchored oligo(dT) primers and 26 arbitrary decamers and nondenaturing gel.

In a preferred embodiment, by comparing the patterns of mRNA expression in cells before and after exposure to BMP, TGF-β or activin, one can identify the genes that are transcriptionally induced or repressed by the corresponding Smad proteins.

RNA Isolation: Although both total RNA or poly(A) RNA can be used for differential display, the frequent high background smear problem associated with the use of poly(A) RNA discourage its use as an RNA source (see below in discussion). Total RNA is the template of choice for differential display also because of its easy isolation and integrity verification by agarose gel. Total cellular RNA isolation can be carried out using either the standard CsCl gradient or a simplified method developed by Chromczynski and Sacchi. The isolated RNA should be stored in diethyl pyrocarbonate (DEPC)-treated $H_2O$ or as an ethanol precipitate at $-80°$, before either Northern blot analysis or DNase I treatment is applied to remove contaminant chromosomal DNA prior to differential display.

DNase I Treatment of Total RNA: Removal of all contaminating chromosomal DNA from the RNA sample is essential before carrying out differential display. 10 to 100 μg of total cellular RNA is incubated with 10 units of human placental ribonuclease inhibitor (BRL, Gaithersburg, Md.), 10 units of DNase I (BRL) in 10 mM Tris-Cl, pH 8.3, 50 mM KCl, 1.5 mM $MgCl_2$ for 30 min at 37° C. DNase I is inactived by adding an equal volume of phenol:chloroform (3:1) to the sample. The suspension is mixed by vortexing and the sample is left on ice for 10 min. The sample is next centrifuged at full speed, for 5 min at 4° C. in an Eppendorf centrifuge. The supernatant is saved and the RNA is ethanol precipitated by adding 3 vol of ethanol in the presence of 0.3 M sodium acetate and incubated at $-80°$ for 30 min. The RNA is pelleted by centrifuging at 4° C. for 10 min. The RNA pellet is rinsed with 0.5 ml of 70% ethanol (made with DEPC-H2O) and the RNA is redissolved in 20 μl of DEPC-treated $H_2O$. The RNA concentration is measured at $OD_{260}$ with a spectrophotometer by diluting 1 μl of the RNA sample in 1 ml of $H_2O$. The integrity of the RNA samples should be checked before and after cleaning with DNase I by running 1–3 μg of each RNA on a 7% formaldehyde agarose gel. The RNA sample can be stored at a concentration higher than 1 μg/μl at $-80°$ C. before use for differential display.

Reverse Transcription of mRNA: A cleaned total RNA sample can be freshly diluted to a concentration of 0.1 μg/μl in DEPC-H2O, set on ice, and the remaining undiluted RNA sample can be immediately frozen to avoid degradation. 4 reverse transcription reactions for each RNA sample is set up in four 0.5-ml PCR tubes; each containing 1 of the 4 different $T_{12}VN$ primers ($T_{12}VG$, $T_{12}VA$, $T_{12}VT$, $T_{12}VC$, where V may be G, A, or C).[9] For a 20-μl reaction, 9.4 μl of $H_2O$, 4 μl of 5× reaction buffer (250 mM Tris-HCl, pH 8.3, 375 mM KCl, 15 mM $MgCl_2$, 50 mM DTT), 1.6 μl of 250 μM each dNTPs, 2 μl of 10 μM $T_{12}MN$ primer, and 2 μl of 0.1 μg/μl DNA-free total RNA are added in order. Alternatively, 12 possible $T_{12}VN$ primers can be used separately in each reverse transcription reaction. The thermocycler can be programed as follows: 65° C. for 5 min, 37° C. for 60 min, 95° C. for 5 min, and soak at 4° C. The cycle is started, and after incubating for 10 min at 37° C. 1 μl (200 units) of Moloney murine leukemia virus reverse transcriptase is added to each tube. At the end of the reverse transcription reaction, the tubes are briefly spun with 1.5-ml adapter tubes to collect condensation. The tubes are set on ice for PCR or stored at $-20°$ C. for later use.

PCR Amplification: [$\alpha$-$^{35}$S]dATP (1200 Ci/mmol) or [$\alpha$-$^{33}$P]dATP is thawed in advance and set on ice. The PCR tubes are labeled to mark the reverse-transcribed cDNA and primer set used. For each primer set combination, 8.2 μl $H_2O$, 2 μl of 10×PCR buffer (100 mM Tris-Cl, pH 8.4, 500 mM KCl, 15 mM $MgCl_2$, 0.01% gelatin), 1.6 μl of 25 μM dNTP, 2 μl of 2 mμM arbitrary primer, 2 μl of 10 μM $T_{12}VN$ primer, 2 μl of corresponding $T_{12}VN$ reverse-transcribed cDNA, 1 μl of [$\alpha$-$^{35}$S]dATP or [$\alpha$-$^{35}$P]dATP, and 0.2 μl (1 unit) of AmpliTaq (Perkin-Elmer) are added in order, at room temperature. By pipetting up and down, the suspension is mixed well and 25 μl of mineral oil is overlayed on top of the reaction mixture. PCR reactions are carried out as follows: 94° C. for 30 sec, 40° C. for 2 min, 72° C. for 30 sec for 40 cycles, 72° C. for 5 min and soak at 4° C.

It is advantageous to prepare batches of core mixes based on the above formula. For example, reverse-transcribed cDNA and arbitrary primers are aliquoted individually, but 10× of the PCR core mix is made for each of the four $T_{12}VN$ primers to be used in combination with five different arbitrary primers for a pair of RNA samples being compared.

Denaturing Polyacrylamide Gel Electrophoresis: 3.5 μl of sample plus 2 μl of loading dye (95% formamide, 0.09% w/v bromophenol blue, and 0.09% w/v xylene cyanole FF) is used and incubated at 80° C. for 2 min before loading onto a 6% DNA sequencing gel. The gel is electrophoresed for about 3 hr at 60 W constant power until the xylene cyanole dye runs to within 10 cm from the bottom. After electrophoresis, the gel is transfered directly onto a piece of Whatman 3MM paper. Next, the gel is covered with a sheet of Saran wrap and dried under vacuum at 80° C. for 1 hr. The Saran wrap is taken off and the X-ray film is exposed at room temperature for 24 to 48 hr. The film is oriented with the dried gel with radioactive ink or needle punches.

Nondenaturing Polyacrylamide Gel Electrophoresis: 3.5 μl of sample is mixed with 2 μl dye solution (20% glycerol, 0.1% bromphenol blue, and 0.1% xylene cyanole FF) and loaded onto a 6% polyacrylamide gel (3×40 cm) without urea. The gel is run at 60 W until the xylene cyanole dye reaches to 5 cm from the bottom. The gel is transfered, dried, and exposed to the X-ray film as above.

Reamplifcation of cDNA Probe: After developing the film, the autoradiogram is aligned with the gel. The bands of interest are located by either marking with a clean pencil underneath the film or cutting through the film. The gel slice is soaked along with the 3MM paper in 100 μl of distilled $H_2O$ for 10 min. The tubeis boiled with a tightly closed cap (e.g., with Parafilm) for 15 min. If the fragment is recovered from a nondenaturing gel, one can omit the ethanol precipitation step. The tube is spun for 2 min to collect condensation and the gel and paper debris is pelleted. The supernatant is transfered to a new microfuge tube. 10 μl of ethanol is added. This is allowed to sit for 30 min on dry ice. To pellet the DNA, the tube is centrifuged for 10 min at 4° C. After centrifugation the white glycogen powder should be visible. The supernatant is discarded and and the pellet rinsed with 200 μl ice-cold 85% ethanol. The pellet is to be left undisturbed. To remove the residual ethanol, the tube is spun briefly. The pellet is dissolved with 10 μl of distilled $H_2O$ and 4 μl is used for reamplification. The rest is saved at $-20°$ C. for future use.

Reamplification is done using the same primer set and PCR conditions except the dNTP concentrations are 20 µM (use 250 µM dNTP stock) instead of 2–4 µM and no isotopes are added. A 40 µl reaction is recommended. Thirty microliters of the reamplified PCR sample is run on a 1.5% agarose gel with xylene cyanole as a loading dye, and stained with ethidium bromide. The remaining PCR samples are saved at −20° C. for cloning or future reamplification. About 90% of probes should be seen after the first round of PCR. If a cDNA probe fails to be amplified in the first round, 4 µl of the PCR sample from the first round can be used as a template for a second round of PCR using identical conditions. Next, the size of a reamplified PCR product is checked to see if it is consistent with its size on the DNA sequencing gel. The reamplified cDNA probe is cut form the agarose gel under a UV lamp and extracted using the Qiaex kit (Qiagen) or purified with a Millipore spin column. The extracted cDNA probe is eluted in 20 µl of $H_2O$ and saved for a probe for Northern blot analysis. If more cDNA probe needs to be reamplified, 4 µl of the original eluted cDNA from the sequencing gel or nondenaturing gel can be used again as a template.

Northern Blot Confirmation: One can use either a cloned or reamplified DNA probe directly for the Northern blot analysis to verify the differential expression of the gene. Generally, 20 µg of each total RNA sample is run on a 7% formaldehyde agarose gel (1.1%) and transferred to a nylon membrane essentially as described. 9 µl of Qiaex extracted probe is labeled with [α-$^{32}$P]dCTP by the random-prime method, except 0.5 µM of the corresponding $T_{12}MN$ primer is included as well as random hexamers. The unincorporated isotope is removed using a Sephadex G-50 spin column. The membrane is prehybridized and hybridized and the standard procedure is followed. The membrane is washed twice for 15 min at room temperature with 1×SSC, 0.1% SDS, and once at 55° for 20 min with 0.25×SSC, 0.1% SDS. The membrane is dried briefly between two sheets of 3 MM paper and exposed to a X-ray film with an intensifying screen at −80° C.

Cloning and Sequencing of cDNA Probe: Reamplified cDNA probes can be cloned into the PRII vector using the TA cloning system from Invitrogen (San Diego, Calif.) or the pCR-TRAP positive-selection cloning system from Gen-Hunter Corporation (Brookline, Mass.). Plasmid DNA sequencing of cloned cDNA probes with either T7 or SP6 primer can be carried out using the Sequenase kit from United States Biochemicals Co. (Cleveland, Ohio) or fmole kit (Promega).

Cloning of Full-Length cDNA: After a cDNA probe is confirmed by Northern blot to give an expected differential display pattern, the cloned cDNA probe can be used to screen a cDNA library for a full-length clone by the standard procedure. If the reamplified cDNA probe before being cloned detects a single mRNA species on the Northern blot, it can be used directly as a probe to screen a cDNA library, bypassing an intermediate cloning step. To recover the 5' upstream sequence of the gene if a cDNA library is unavailable, one can also use the 5' RACE method based on sequence information for the cloned cDNA probe generated by differential display.

Automatic Analysis of Differential Display Pattern:

If cloning of differentially expressed genes is not the first priority and a diagnostic pattern is required instead, it is advantageous to use a nonradioactive detection method in combination with automatic analysis of the resulting gel pattern.

Sequencing: For this purpose, an automatic DNA sequencing machine can be used with denaturing or nondenaturing gel electrophoresis. Arbitrary primers are labeled with fluorescent dyes FAM, JOE, ROX, and TAMRA (Applied Biosystems) according to the manufacturer's instruction. Since the fluorescence intensity of FAM and JOE is four to sixfold higher than that of ROX and TAMRA, it is difficult to use all four dyes for the comparison of four different RNA samples in a single lane. In addition, different dyes have different effects on the hybridization property of the primer labeled. At the moment, only FAM or JOE is used to label the arbitrary primer so samples should be compared side by side as described in the standard procedure above.

For each reaction, 10 µl $H_2O$, 2 µl of 10×PCR buffer (as above)), 2 µl of 1 mM dNTP, 2 µl of 25 µM arbitrary primer (dye labeled and HPLC purified), 2 µl of 5 µM anchored oligo(dT) primer, 2 lµ of respective reverse-transcribed cDNA, and 0.2 µl (1 unit) of AMpliTaq (Perkin-Elmer)is added at room temperature. PCR reactions are carried out as described above. It is also advantageous to prepare core mixes as above. To avoid high background and to achieve maximal sensitivity, the amount of sample should be adjusted to achieve relative band intensities between 200 and 1000 arbitrary units in the case of the ABI machine. The electrophoretic runs are recorded and band patterns are compared according to the software instructions of the manufacturer.

ii. Affymetrix Chips:

Another assay to monitor the activity of TGF-β signaling pathways in individual cells is using Affymetrix chips. In this assay, the expression of thousand of TGF-beta pathway genes can be rapidly monitored by hybridization of fluorescently labeled cDNA to a high density oligonucleotide array (see D. J. Lockhart et al., "Expression monitoring by hybridisation to high-density oligonucleotide arrays," Nat. Biotech. 14: 1675, 1996 and U.S. Pat. No. 5,556,752 hereby incorporated by reference). Libraries of unimolecular, double-stranded oligonucleotides on a solid support have proved to be useful in pharmaceutical discovery for the screening of lead biological compounds for specific interactions between double-stranded oligonucleotides, and peptides, proteins, drugs. The probes are restricted in their movement and flexibility using double-stranded oligonucleotides as scaffolding.

In a preferred embodiment, the combined use of photolithography and oligonucleotide chemistry is used to synthesize an array of as many as 400,000 different oligos on a 1.6 $cm^2$ glass slide. Each mRNA is represented by 10 pairs of oligonucleotides, each pair consisting of one oligo that matches a 20 bp segment of the transcript, and a control oligo that contains a centrally located 1 bp mismatch. The concentration of each mRNA in a sample is indicated by the intensity of fluorescent DNA probe hybridized to the corresponding wild-type oligos relative to the mutant control oligos. By comparing the patterns of transcript expression in cells before and after brief exposure to BMP, TGF-beta, or activin, it is possible to identify individual genes that are transcriptionally induced or repressed by the corresponding Smad proteins. The method is able to unambiguously detect mRNAs that are present at a frequency of of 1 per 300,000, and is quantitative over a thousand fold concentration range. RNA preparation for hybridization: Labeled RNA is prepared from clones containing a T7 RNA polymerase promoter site by incorporating labeled ribonucleotides in an in vitro transcription(IVT) reaction. Either biotin-labeled or fluorescein-labeled UTP and CTP (1:3 labeled to unlabeled) plus unlabeled ATP and GTP is used for the reaction with 2500 U of T7 RNA polymerase. Following the reaction, unincorporated nucleotide triphosphates arre removed using a size-selective membrane (Microcon-100, Amicon, Beverly, Mass.). The total molar concentration of RNA is based on a measurement of the absorbance at 260 nm. Following quantitation of RNA amounts, RNA is fragmented randomly to an average length of approximately 50 bases by heating at 94° C. in 40 mM Tris-acetate pH 8. 1, 100 mM potassium acetate, 30 mM magnesium acetate, for 30 to 40 min. Fragmentation reduces possible interference from RNA secondary structure, and minimizes the effects of multiple interactions with closely spaced probe molecules. For material made directly from cellular RNA, cytoplasmic RNA is extracted from cells, and poly $(A)^+$ RNA is isolated with an oligo dT selection step (PolyAtract, Promega, Madison, Wis.). RNA is then amplified. One microgram of poly $(A)^+$ RNA is converted into double-stranded cDNA using a cDNA synthesis kit (Life Technologies, Gaithersburg, Md.) with an oligo dT primer incorporating a T7 RNA polymerase promoter site. After second-strand synthesis, the reaction mixture is extracted with phenol/chloroform, and the double-stranded DNA is isolated using a membrane filtration step (Microcon-100, Amicon). Labeled cRNA is made directly from the cDNA pool with an IVT step as described above. The total molar concentration of labeled cRNA is determined from the absorbance at 260 nm and assuming an average RNA size of 1000 ribonucleotides. It is convenient to use the convention that 1 OD is equivalent to 40 μg of RNA is used, and that 1 μg of cellular mRNA consists of 3 poll of RNA molecules. Cellular mRNA is also labeled directly without any intermediate cDNA synthesis steps. Poly $(A)^+$ RNA is fragmented as described, and the 5' ends of the fragments are kinased and then incubated overnight with a biotinylated oligoribonucleotide (5'-biotin-AAAAAA-3') in the presence of T4 RNA ligase (Epicentre Technolgies, Madison, Wis.). Alternatively, mRNA is also labeled directly by UV-induced cross-linking to a psoralen derivative linked to biotin (Schleicher & Schuell, Keene, N.H.).

Array hybridization and scanning: The hybridization solution typically contains 0.9 M NaCl, 60 mM $NaH_2PO_4$, 6 mM EDTA, and 0.005% Triton X-100, is adjusted to pH 7.6 (referred to as 6×SSPE-T). In addition, the solutions can contain 0.5 mg/ml unlabeled, degraded herring sperm DNA (Sigma, St. Louis, Mo.). Prior to hybridization, RNA samples are heated in the hybridization solution to 99° C. for 10 min, placed on ice for 5 min, and allowed to equilibrate at room temperature before being placed in the hybridization flow cell. Following hybridization, the solutions are removed, the arrays are washed with 6×SSPE-T at 22° C. for 7 min, and then washed with 0.5×SSPE-T at 40° C. for 15 min. When biotin-labeled RNA is used, the hybridized RNA is stained with a streptavidin-phycoerythrin conjugate (Molecular Probes, Eugene, Oreg.) prior to reading. Hybridized arrays are stained with 2 μg/ml streptavidin-phycoerythrin in 6×SSPE-T at 40° C. for 5 min. The arrays are conveniently read using a scanning confocal microscope made for Affymetrix by Molecular Dynamics (Commercially available through Affymetrix, Santa Clara, Calif.). The scanner uses an argon ion laser as the excitation source, with the emission detected by a photomultiplier tube through either a 530 nm bandpass filter (fluorescein) or a 560 nm longpass filter (phycoerythrin). Nucleic acids of either sense or antisense orientations can be used in hybridization experiments. Arrays with probes for either orientation (reverse complements of each other) are made using the same set of photolithographic masks by reversing the order of the photochemical steps and incorporating the complementary nucleotide.

Quantitative analysis of hybridization patterns and intensities: Following a quantitative scan of an array, a grid is aligned to the image using the known dimensions of the array and the corner control regions as markers. The image is reduced to a simple text file containing position and intensity information using software developed at Affymetrix (available with the confocal scanner). This information is merged with another text file that contains information relating physical position on the array to probe sequence and the identity of the RNA (and the specific part of the RNA) for which the oligonucleotide probe is designed. The quantitative analysis of the hybridization results involves a simple form of pattern recognition based on the assumption that, in the presence of a specific RNA, the PM probes will hybridize more strongly on average than their MM partners. The number of instances in which the PM hybridization signal is larger than the MM signal is computed along with average of the logarithm of the PM/MM ratios for each probe set. These values are used to make a decision (using a predefined decision matrix) concerning the presence or absence of an RNA. To determine the quantitative RNA abundance, the average of the differences (PM minus MM) for each probe family is calculated. The advantage of the difference method is that signals from random cross-hybridization contribute equally, on average, to the PM and MM probes, while specific hybridization contributes more to the PM probes. By averaging the pairwise differences, the real signals add constructively while the contributions form cross-hybridization tend to cancel. When assessing the differences between two different RNA samples, the hybridization signals from side-by-side experiments on identically synthesized arrays are compared directly. The magnitude of the changes in the average of the difference (PM-MM) values is interpreted by comparison with the results of spiking experiments as well as the signals observed for the internal standard bacterial and phage RNAs spiked into each sample at a known amount. Data analysis programs developed at Affymetrix perform these operations automatically.

iii. Serial Analysis of Gene Expression (SAGE):

SAGE is another technique that allows a rapid, detailed analysis of thousands of transcripts. SAGE is based on two principles. First, a short nucleotide sequence tag [9 to 10 base pairs (bp)] contains sufficient information to uniquely identify a transcript, provided it is isolated from a defined position within the transcript. For example, a sequence as short as 9 bp can distinguish 262,144 transcripts given a random nucleotide distribution at the tag site, whereas current estimates suggest that even the human genome encodes only about 80,000 transcripts. Second, concatenation of short sequence tags allows the efficient analysis of transcripts in a serial manner by the sequencing of multiple tags within a single clone. As with serial communication by computers, wherein information is transmitted as a continuous string of data, serial analysis of the sequence tags requires a means to establish the register and boundaries of each tag.

Double-stranded cDNA is synthesized from mRNA by means of a biotinylated oligo(dT) primer. The cDNA is then cleaved with a restriction endonuclease (anchoring enzyme) that can be expected to cleave most transcripts at least once. Typically, restriction endonucleases with 4-bp recognition sites are used for this purpose because they cleave every 256 bp on average, whereas most transcripts are considerably larger. The most 3' portion of the cleaved cDNA is then isolated by binding to streptavidin beads. This process provides a unique site on each transcript that corresponds to the restriction site located closest to the polyadenylated [poly(A)] tail. The cDNA is then divided in half and ligated via the anchoring restriction site to one of two linkers containing a type IIS (tagging enzyme). Type IIS restriction endonucleases cleaves at a defined distance up to 20 bp away from their asymmetric recognition sites. The linkers are designed so that cleavage of the ligation products with the tagging enzyme results in release of the linker with a short piece of the cDNA.

For example, a combination of anchoring enzyme and tagging enzyme that would yield a 9-bp tag can be cured. After blunt ends are created, the two pools of released tags are ligated to each other. Ligated tags then serve as templates for polymerase chain reaction (PCR) amplification with primers specific to each linker. This step serves several purposes in addition to allowing amplification of the tag sequences. First, it provides for orientation and punctuation of the tag sequence in a very compact manner. The resulting amplification products contain two tags (one ditag) linked tail to tail, flanked by sites for the anchoring enzyme. In the final sequencing template, this results in 4 bp of punctuation per ditag. Second and most importantly, the analysis of ditags, formed before any amplification steps, provides a means to completely eliminate potential distortions introduced by PCR. Because the probability of any two tags being coupled in the same ditag is small, even for abundant transcripts, repeated ditags potentially produced by biased PCR can be excluded from analysis without substantially altering the final results. Cleavage of the PCR product with the anchoring enzyme allows for the isolation of ditags that can then be concentrated by ligation, cloned, and sequenced.

In addition to providing quantitative information on the abundance of known transcripts, SAGE can be used to identify novel TGF-beta pathway expressed genes. SAGE can provide both quantitative and qualitative data about gene expression. The combination of different anchoring enzymes with various recognition sites and type IIS enzymes with cleavage sites 5 to 20 bp from their recognition elements lends great flexibility to this strategy. It is envisioned that one major application of SAGE will be comparison of gene expression patterns in various TGF-beta associated developmental and disease states.

b. Animals

In addition to tests on cells in culture or embryonic cells, agonists or antagonists of Smad-DNA binding assays can be tested in whole animal models. These include but are not limited to:
1. Diabetic renal disease in rodents where it has been shown that neutralising antibodies to TGF-β have an attenuating affect.
2. Repair of segmental fractures or other bone healing where it has been previously shown that application of BMPs enhance healing.
3. Reduction in scaring in animal models where it has been shown that neutralizing antibodies to TGF-β reduce scarring.
4. Inhibition of breast cancer cell tumorigenicity in rodent models where it has been shown that neutralizing antibodies to TGF-β inhibit tumorigenicity.
5. Suppression of intimal hyperplasia in a rodent model in which neutralizing antibodies to TGF-β have a suppressing effect.
6. Reversal of age or steroid impaired wound healing where it has been shown that that administration of TGF-β has an effect.
7. Enhancement of muscle mass in a rodent model where it has been shown that absence of the TGF-β superfamily member GDF-8 causes additional muscle mass (Mcpharron, Lawley and Lee (1997) Nature, 387: 83–90).

Other models are known to those experienced in the art and others will be generated in the future for example by production of transgenic animals or knockout mutant animals. Thiese animal models provide distinct, tissue specific responses to different different members of the TGF-β superfamily of ligands. Agonists or antagonists identified in the assays may alter one or more of these responses.

2. Screens to Identify cis-regulatory DNA Sequences and Clone Genes that Are Directly Regulated or Controlled by TGF-β Pathways a. One-hybrid Screen.

A yeast one-hybrid system can also be used to identify cis-regulatory sequences that are bound by a specific transcription factor. In this particular application, the one-hybrid system employs a reporter gene that confers growth under conditions of starvation for a particular nutrient, usually an amino acid such as histidine. A library of genomic DNA fragments is created by insertion upstream of the reporter gene's basal promoter and a large pool of plasmid transformants (usually controlled by $\geq 10^6$ clones) is screened for growth that is dependent upon conditional expression of the transcription factor in question. The DNA binding domain of the transcription factor of interest is fused to a nuclear localization signal and an activation domain from GAL4, and the hybrid protein is expressed under control of a galactose-inducible promoter. Clones that grow on Gal(+) His(−) may result from insertion of a DNA sequence that is bound specifically by the hybrid protein. The resulting plasmids can be recovered from yeast and transformed into E. Coli. The resulting clones can be sequenced and used as probes as a means of determining whether they indeed contain binding sites for the transcription factor in question, and to identify the most proximal genes.

In a preferred embodiment, a Smad-MH1 DNA binding domain can be used in this scheme to screen for genomic DNA sequences capable of functioning as a Smad responsive cis regulatory element in yeast. A significant number of clones from a round of one-hybrid screening with the Drosophila Ubx protein were found to contain Ubx binding sites and to lie near Ubx-regulated genes b. Immunoprecipitation of Smad-DNA Complexes In one embodiment, DNA sequences bound by MAD or Smad proteins in cells can be purified by immunoprecipitation of these complexes from fragmented chromatin with an antibody that recognizes the Smad or an attached epitope tag. This approach has been used to identify targets of the Drosphila homeotic protein Ubx (see Gould et al., Nature 348: 308–312, 1990). Essentially, the nuclei are isolated by centrifugation of cell lysates generated by gentle disruption in a buffer containing a nonionic detergent such as Triton-X 100. The nuclei are resuspended in 10 mM HEPES buffer pH 7.9, 10 mM KCl, 2 mM $MgCl_2$, 0.5 mM DTT, 15 µg/ml aprotinin, 5 µg/ml leupeptin, 2 µg/ml pepstatin and 0.5 mM PMSF. Chromosomal DNA is digested, either by adding 1 mM $MgCl_2$ and $10^4$ Units of HaeIII and incubating for 30 min, or by adding 0.5 mM $CaCl_2$ and 16 units of micrococcal nuclease (Sigma) followed by 5 min incubation on ice, terminated with 2.5 mM EGTA. Then, the soluble DNA-protein complex is isolated by centrifugation at 1,500 g for 2 min, and the pellet resuspended in TEP (12 mM Tris-based neutralized to pH 7.5 with 3 mM EDTA free acid, 15 µg/ml aprotinin, 5 µg/ml leupeptin, 2 µg/ml pepstatin and 0.5 mM PMSF) to release soluble chromatin. Following 15 min incubation and centrifugation at 1,500 g for 5 min, NaCl and BSA are added to the released supernatant to 100 mM and 1 mg/ml, respectively. After centrifugation at 130,000 g for 20 min, the supernatant is preabsorbed for 20 min with 200 µl of streptavidin-agarose beads (Sigma).

Preabsorbed chromatin is incubated with or without 10 µg/ml biotinylated antibody directed against a Smad or epitope tag for 45 min and then with 40 µl of streptavidin-agarose for 30 min. Beads are washed in TEP+100 mM NaCl before either protein (Western blot analysis), or DNA analysis. The cloning and analysis of purified DNAs can be performed as described above for DNAs identified in a one-hybrid screen.

For cultured cells and Drosophila embryos, photocrosslinking with UV light is first done to stabilize protein-DNA complexes prior to immunoprecipitation. Essentially, nuclei are isolated from 5–15 old embryos in the presence of bivalent cations (5 mM $Mg^{2+}$ and 2 mM $Ca^{2+}$) and 0.5 M hexalyne-glycol.

Generation of Protein—DNA Adducts

UV crosslinking can be performed as described by Gilmour and Lis (1985). Nuclei are irradiated for 10 min at 4° C. under a germicide UV (254 nm) lamp delivering 4×10⁴ erg/cm2/s. After lysis in 4% lauryl-sarcosine, CsCl is added to a final density of 1.3. The proteins floating at the surface are eliminated after centrifugation for 10 min at 20,000 g. The DNA is sheared by 10 passages through 1 mm diameter needle and loaded on the bottom of a CsCl step density gradient (1.3, 1.5, and 1.7). The gradient is centrifuged for 17 h at 55,000 r.p.m. at 20° C. in a 75 Ti rotor. The DNA fractions are pooled, dialysed twice against 2 L of dialysis buffer (10 mM Tris, 100 mM NaCl, 1 mM EDTA and 0.5 mM PMSF, pH 7.5), ethanol precipitated and resuspended in EcoRl digestion buffer. Digestion is performed in the presence of 0.8% NP 40 (10 units per mg of DNA, three times for 2 h each).

Immunoselection and Cloning of Mad-protein Adducts

EcoR1 digested samples are preincubated for 1 h at 4° C. through a column of protein A-Sepharose beads coupled to a (monoclonal) antibody against a Smad protein or epitope tag, in the presence of an excess of yeast-tRNA to avoid non-specific binding of DNA. Sepharose beads are washed three times each with buffer (10 mM Tris, 0.5 M LiCl, 0.1% SDS and 2% NP40, pH 7.4) and with buffer II (50 mM Tris and 50 mM NaCl, pH 8.0). The immunoprecipitate is eluted with 4% lauroyl-sarcosine, dialysed against 10 mM Tris buffer (pH 7.4). $^{32}$P-labelled insert DNA (10 ng per clone) and 1 mg of sonicated herring sperm DNA is added, and the incubation continued for 45 min. 100 mgs of monoclonal antibody against a Smad protein conjugated to Trisacryl beads (IBF) is added to the binding reaction. After 90 min incubation, the beads are washed three times with the binding buffer and the DNA is released by a stepwise increase of the salt concentration in the same buffer. The various fractions are analysed by electrophoresis on agarose gel (0.8%) and autoradiography.

C. Affinity Purification of Smad-DNA Complexes

In another embodiment, DNA sequences bound by a MAD or Smad protein in vitro can be purified by immobilizing or precipitating the MAD or Smad protein. A MAD or Smad protein can be immobilized or precipitated by attachment to a resin by means of: (a) a fused protein that can be affinity purified (e.g., maltose binding protein (New England Biolabs) or Glutathione S Transferase (Pharmacia Biotech), hexa-histidine, (b) an antibody directed against the MAD or Smad protein, (c) an antibody directed against an epitope tag (e.g., Kodak FLAG epitope tag).

From a pool of fragments created by restriction endonuclease digestion or by shearing of genomic DNA, DNA fragments that are specifically bound by a MAD or Smad protein are retained during washes that remove free DNA. Bound DNA can then be cloned and analyzed, or subjected to ligation-mediated PCR and another round of enrichment by binding to immobilized MAD or Smad. By repetition of the selection-amplification cycle, it is possible to enrich the extent necessary for adequate purification of DNA fragments with high affinity Smad binding sites. Cloning and analysis of purified DNAs can be performed as described for DNAs identified in the one-hybrid screen.

EXPERIMENTAL

The following examples serve to illustrate certain preferred embodiments and aspects of the present invention and are not to be construed as limiting the scope thereof. In the experimental disclosure which follows, the following methodology apply:

Generation of MAD clones: Mitotic clones homozygous for the Mad$^{1.2}$ allele were generated by heat-shock induction of FLP recombinase in the progeny of w; Mad$^{1.2}$, P[ry+, hs-neo, FRT] 40A/CyO males (stock provided by V. Wiersdorff, M. Mlodzik, and S. Cohen) crossed to w1118, hsFLP1; P[w+, hs-pM] 36F, P[ry+, hs-neo, FRT] 40A female flies (T.Xu & G. M. Rubin, *Development*, 117:1223–1237).

Immunohistochemistry: Antibody staining of imaginal discs was performed as previously described (Williams et al., 1993). Wing imaginal discs were dissected, fixed, and stained with antibodies. The following experimental steps were performed at 4° C. Imaginal disc complexes dissected in phosphate-buffered saline (pH 7.0) were fixed for 30 min in fixative (0.1M PIPES [pH 6.9], 150 mM NaCl, 1 mM EGTA [pH 6.9], 1% Triton X-100, 2% formaldehyde). The fixed disc complexes were incubated for 6 hr in block buffer (50 mM Tris [pH 6.8], 150 mM NaCl, 0.5% NP-40, 5 mg/ml BSA). The disc complexes were incubated with primary antbodies overnight in wash buffer (50 mM Tris [pH 6.8], 150 mM NaCl, 0.5% NP-40, 1 mg/ml BSA). The disc complexes were washed four times for 20 min each with the wash buffer and incubated with secondary antibodies for 3 hr. When biotin-labeled secondary antibodies were used, the disc complexes were washed four times again for 15 min each with the wash buffer and incubated for 2 hr with streptavidin-conjugated fluorophores diluted with the wash buffer (1:100). The disc complexes were washed four times for 15 min each with the wash buffer and soaked overnight in mounting solution (50 mM Tris [pH 8.8], 150 mM NaCl, 30% glycerol [v/v]). The wing discs were dissected and mounted in the mounting solution. When an FITC-conjugated reagent was used, 0.5 mg/ml of p-phenylethylene diamine (Sigma) was added to the mounting soulution. Confocal images were collected with a Bio-Rad MRC-600 laser scanning confocal microscope (Bio-Rad Microscience) and assembled with Abode Photoshop 2.5 Abode Systems) using a Macintosh Quadra 950 microcomputer and methods described previously.

Production and Purification of MAD (SMAD) Fusion Proteins:

For fusions containing domain 1 (MAD and MAD$^N$) a Bam HI site was introduced by PCR 15 bp upstream of the predicted initiator ATG. Fusion of this Bam HI site to a Bam HI polylinker site at the C-terminus of GST or MBP resulted in insertion of the sequence Gly-Ser-Ser-Asn-Arg between GST (or MBP) and MAD. The full length MAD fusions contained MAD sequences extending from the Bam HI site to a Hind III site located within the 3' UTR. MAD$^N$ was truncated at a Pvu II site located 720 bp 3' of the initiator ATG. MAD$^C$ was constructed by first cloning a 1043 bp Pst I fragment of the Mad cDNA into pBluescript KS+ and then fusion to GST as a Bam HI-Eco RI fragment. The R107C point mutation was introduced into the MAD coding region by single primer site-directed mutagenesis, and was confirmed by sequencing. *E. coli* DH5α strains harboring the GST fusion constructs were grown at 37° C. to an OD$_{650}$ of 0.5, shifted to 30° C. and grown to an OD$_{650}$ of 0.6, and IPTG added to a final concentration of 0.5 mM to induce the expression of the fusion proteins. The cells were grown for another 2,5 hours at 30° C., harvested, and resuspended in sonication buffer (25 mM Tris [pH 7.5], 0.3 M KCl, 12.5 mM MgCl$_2$, 0.1% NP40, 1 mM DTT, 10% Glycerol, 0.1 mg/ml PMSF, 1 mg/ml aprotinin, 1 mg/ml leupeptin, 1.5 1 mg/ml pepstatin). The cells were sonicated 10 times for 20 sec at 65% power at 30 sec intervals on ice. The supernatant from the lysate was recovered by centrifugation at 20,000×g for 20 min and incubated with glutathione-Sepharose (Pharmacia) for 1 hr. at 4° C. with gentle agitation. The beads were sedimented by centrifugation at 500×g for 5 min, washed twice with the sonification buffer, four times with wash buffer (25 mM Tris [pH 7.5], 50 mM NaCl, 5 mM MgCl$_{2,1}$ mM DTT, 10% Glycerol, 0.1 mg/ml PMSF, 1 mg/ml aprotinin, 1 mg/ml leupeptin, 1.5 mg/ml pepstatin) at 4° C. The sedimented beads were then incubated with elution buffer (same as the wash buffer except 10 mM final glutathione was added) for 30 min at 4° C. The beads were pelleted and the supernatant was dialyzed four times for 4 hrs each in a liter of dialysis buffer (same as the wash buffer without protease inhibitors) at 4° C. Proteins were aliquoted, frozen in liquid nitrogen, and stored at −80° C. MBP fusion proteins were prepared according to the protocol for GST fusions except for the following changes. Lysis buffer for MBP fusions was 20 mM Tris pH 7.5, 200 mM NaCl, 1 mM EDTA, plus the same cocktail of protease inhibitors for GST fusions. After clearing by centrifugation, MBP fusion lysates were absorbed to amylose-coupled sepharose (New England BioLabs), the resin was washed with 20 mM Tris pH 7.5, 200 mM NaCl, mM EDTA and fusion protein was eluted with wash buffer plus 10 mM maltose. Purified fusion proteins were dialyzed for 2 hrs in 25 mM Tris pH 7.5/50 mM NaCl/5 mM $MgCl_2$/10% glycerol/0.5 mM DTT, aliquoted and stored frozen in at −80° C.

Gel Mobility Shift Assay:

Affinity purified MAD proteins were incubated with DNA probes ($2 \times 10^4$ cpm per reaction, 5' end labeled with [$\gamma$-$^{32}$P] ATP [6000 Ci/mmole, NEN] and T4 polynucleotide kinase) in binding buffer (25 mM Tris [pH 7.5], 80 mM NaCl, 35 mM KCl, 5 mM $MgCl_2$, 1 mM DTT, 10% glycerol [v/v], 50 μg/ml poly (dI.dC), 50 μg/ml poly (dA.dT), 150 μg/ml non-specific competitor DNA[random double-stranded oligonucleotides or sonicated salmon sperm DNA]) for 20 min at room temperature. Binding reactions for FIG. 2 and 3 contained 3.3 μg/ml poly (dI.dC) without other nonspecific competitor DNA. The binding reaction mixtures were subjected to low ionic strength (22.5 mM Tris base, 22.5 mM boric acid) electrophoresis in 5% polyacrylamide gels. Autoradiographic images of dried gels were generated with a Molecular Dynamics Phosphor Imager and this data was used for quantitative analyses of binding affinity. Relative binding affinitites were based on bound probe/total probe ratios. The top strands of the double-stranded oligonucleotide probes used were:

$Q^+$ (SEQ ID NO:22): TTTGTGCTTGGCTGCCGTCGCGATTCGACAACTTTGG $Q^m$ (SEQ ID NO:23): TTTGTGCTTGAGATCTAGATCTATTCGACAACTTTGG

UI (SEQ ID NO:24): TTTCTGGACTGGCGTCAGGCCGGCGCTTCCAGCTGCCAAAT

UII (SEQ ID NO:25): AGCTGCCAAATTGCTGCTTTATTAGCTGCGTAAGTGGCTC

Vg (SEQ ID NO:26): CTTGGCTGCCGTCGCGATTC lab-A (SEQ ID NO:27): TACGGGCTGCCGTGGGAGACACCA lab-B (SEQ ID NO:28): CCAGAGCTGTGTAGCAAGAA lab-C (SEQ ID NO:29): GAATCGTATCGAACGGCGGCACTC Ubx-A (SEQ ID NO:5): GCCTGACGCCAGTCCAGAAAC Ubx-B (SEQ ID NO:7): GGAAGCGCCGGCGCTGACGCC Ubx-C (SEQ ID NO:30): CCGGCGCTTCCAGCTGCCAAAT DNaseI Footprinting Assay:

Oligonucleotide primers corresponding to various region of the vg quadrant enhancer and lab midgut enhancer sequences were labeled with [$\gamma$-$^{32}$P] ATP [6000 Ci/mmole, NEN] and T4 polynucleotide kinase, separated from the unincorporated radionucleotides by 12% polyacrylamide gel electrophoresis, and eluted from the gel. PCR reactions were performed to synthesize the probe DNAs with pairs of a $^{32}$P-labeled primer and an unlabeled primer. The PCR products were purified using Qiagen PCR Purification Columns (Qiagen Inc.). The labeled probe DNAs ($1 \times 10^4$ cpm per binding reaction) were incubated with affinity purified GST-$MAD^N$ proteins for 20 min at room temperature in the binding buffer used for the gel mobility shift assay. Binding reactions for the footprint in FIG. 1a contained 5 μg/ml poly (dI.dC) without other non-specific competitor DNA. DNase I solution was added (0.6 volumes of the binding reaction) and incubated for 2 min at room temperature. The DNase I solution was prepared by diluting the DNase I (10 units/ml, Boehringer Mannheim)6–12×$10^4$-fold in DNase I dilution buffer (25 mM Tris [pH7.5], 30 mM NaCl, 20 mM KCl, 1 mM DTT, 8 mM $CaCl_2$, 16 mM $MgCl_2$, 100 μg/ml BSA). The reactions were stopped by adding SDS (final conc. 0.5%) and EGTA (final conc. 25 mM). The reaction mixtures were extracted with phenol/chloroform (1:1 ratio) and then with chloroform. The DNA was recovered by ethanol precipitation, resuspended in TE, and analyzed on sequencing gels. Unlabeled primers identical with the $^{32}$P-labeled PCR primers were used to generate the sequencing ladder of the PCR product.

Reporter Gene Construction

The mutated vg quadrant enhancer DNA used to generate transgenic fly lines was prepared by PCR. The vg quadrant enhancer DNA cloned in the pBlueScript II-KS vector (Stratagene) was used for the PCR templates. The 230 bp fragment from the 5' end to the MAD binding sites was PCR-amplified with SK811F oligonucleotide as the forward primer and Q1 oligonucleotide as the backward primer. The SK811F primer sequence is (SEQ ID NO:31) CAG CTA TGA CCA TGA TTA CGC CAA GC, which corresponds to the sequences around the initiation codon of the β-galactosidase gene in pBlueScript vectors. The Q1 primer sequence is (SEQ ID NO:32) CCAAAGTTGTCGAATA-GATCTGGCAGCCAAGCACAAA The 576 bp fragment from the $MAD^N$ binding site to the 3' end was PCR-amplified with the Q2 oligonucleotide as the forward primer and the SK615B oligonucleotide as the backward primer. The Q2 primer sequence is (SEQ ID NO:33) TTT GTG CTT GAG ATC TGT CGC GAT TCG ACA ACT TTG G while the SK615B primer sequence is (SEQ ID NO:34) GCG TAA TACGAC T CA CTA TAG GGC GA, which is the sequence around the T7 promoter region in pBlueScript II vectors. The PCR products with the SK811F/Q1 and Q2/SK615B primer pairs were digested with Kpn I/Bgl II and with Bgl II/Not I restriction endonucleases, respectively. Two of these ingested fragments were isolated in agarose gel and ligated together into the Kpn I/Not I sites of the hsp-lacZ-CaSpeR fly transformation vector (Nelson & A. Laughon, *Roux Arch. dev. Biol.* 202:341–354, 1993). A portion of the PCR amplified fragments were sequenced to confirm the sequences. The resulting pyramid was injected into Drosophila embryos to generate the transgenic lines using standard techniques(G. M. Rubin, & A. C. Spralding, *Science* 218:348–353 (1982).

EXAMPLE 1

In this example, data is generated that suggests that MAD is required for vg activation in the developing wing blade In the Drosophila wing imaginal disc, signaling from both the anteroposterior (A/P) and dorsoventral (D/V) compartment boundaries are required for appendage formation (S. Blair, "Compartments And Appendage Development In Drosophila," *BioEssays* 17:229–309, 1995). Growth and patterning along the A/P axis depends upon the sequential organizing activities of the engrailed (EN), hedgehog (HH), and decapentaplegic (DPP) proteins (K. Basler and G. Struhl, "Compartment Boundaries And The Control Of Drosophila Limb Pattern By Hedgehog Protein," *Nature* 368:208–214 , 1994; T. Tabata and T. Kornberg, "Hedgehog Is A Signaling Protein With A Key Role In Patterning Drosophila Imaginal Discs," Cell 76:89–102, 1994; Zecca et al., "Sequential Organizing Activities Of Engrailed, Hedgehog and Decapentaplegic in the Drosophila Wing," *Development* 121:2265–2278 (1995); W. Ingham and M. J. Fietz, "Quantitative Effects Of Hedgehog And Decapentaplegic Activity On The Patterning Of The Drosophila Wing," *Curr. Biol.* 5:432–440 1995). The DPP protein acts as a morphogen from its source to organize wing growth, A/P pattern, and to activate gene expression over a long range (W. Ingham and M. J. Fietz, "Quantitative Effects Of Hedgehog And Decapentaplegic Activity on the Patterning Of The Drosophila Wing," *Curr. Biol.* 5:432–440, 1995; L. Poskony et al., "Wing Formation In *Drosophila Melanogaster* Requires Decapentaplegic Gene Function Along The Anterior-posterior Compartment Boundary," *Mech. Dev.* 33:69–82, 1991; Capdevilla, J. & Guerrero, I., "Targeted expression of the signalling molecule decapentaplegic induces pattern duplications and growth alterations in Drosophila wings, "*EMBO J.* 13, 4459–4468, 1994; Nellen, D et al ". Direct and Long-Range Action of A Dpp Morphogen Gradient," *Cell* 85, 357–368, 1996; Lecuit, T et al, "Two distinct mechanisms for long-range patterning by Decapentaplegic in the Drosophila wing," *Nature* 381, 387–393, 1996; Kim., J. et al, "Integration of positional signals and regulation of wing formation and identity by *Drosophila vestigial* gene.," *Nature* 382, 133–138, 1996). Immunohistochemical staining experiments showed the DPP-regulated genes, spalt (sal)(de Celis, J. Fet et al, "A gene complex acting downstream of dpp in Drosophila wing morphogenesis," *Nature* 381, 421–424, 1996) and optomotor-blind (omb), (Grimm, S. & Pflugfelder, G. O.," Control of the gene optomotor-blind in Drosphila wing development by decapentaplegic and wingless," *Science*, 271, 1601–1604, 1996), are expressed in nested patterns centered on and extending up to 20 cell diameters away from the stripe of DPP expression, (Nellen, D et al ".Direct and Long-Range Action of A Dpp Morphogen Gradient," *Cell* 85, 357–368 (1996); Lecuit, T et al, "Two distinct mechanisms for long-range patterning by Decapentaplegic in the Drosophila wing," *Nature* 381, 387–393, 1996) whereas the vestigial (vg) gene is more broadly expressed and is required in all cells of the developing wing. vg activation is regulated by signals from both axes through separate cis-regulatory elements that control complementary patterns of gene expression (Kim., J. et al, "Integration of positional signals and regulation of wing formation and identity by *Drosophila vestigial* gene," "*Nature* 382, 133–138, 1996). The "boundary" enhancer is activated along the D/V boundary via components of the Notch pathway while the "quadrant" enhancer is activated in the remainder of the developing wing blade by DPP as well as a signal from the D/V boundary (Kim., J. et al, "Integration of positional signals and regulation of wing formation and identity by *Drosophila vestigial* gene," "Nature 382, 133–138, 1996). Since, MAD is known to be an intracellular signal transducer downstream of DPP receptors, the requirement of MAD activity for VG expression was examined in the wing imaginal disc in mitotic clones with reduced MAD function. Homozygous clones for the strong Mad$^{1.2}$ allele in developing wing blade cells had significantly reduced levels of VG expression and showed a growth disadvantage in comparison with heterozygous or wild type cells. In contrast, the Mad$^{1.2}$ clones along the D/V boundary did not show any changes in VG expression levels. The different effects of reduction of MAD activity in D/V boundary versus wing blade clones is explained by different regulatory elements that control expression of the vg gene in these regions. This example indicated that the quadrant enhancer clearly requires MAD function and DPP signaling (Kim., J. et al, "Integration of positional signals and regulation of wing formation and identity by *Drosophila vestigial* gene," "*Nature* 382, 133–138, 1996), whereas MAD has no effect on the Notch-dependent D/V boundary enhancer).

EXAMPLE 2

In this example, binding of MAD$^N$ protein to the vg quadrant enhancer is shown to be sequence-specific and essential for activation in vivo.

Smad family members share highly conserved amino- and carboxy-terminal domains 1 and 2 (C. Savage et al., "W. Elegans Genes Sma-2, Sma-3 and Sma-4 Genes Define A Conserved Family Of TGF-beta pathway Components," *Proc. Natl. Acad. Sci. USA* 93:790–794, 1996) which are separated by a less conserved proline-rich linker region. In this example, to investigate whether MAD exerts a direct effect on vg transcription, the ability of different domains of MAD to bind specifically to the quadrant enhancer was tested. MAD-DNA binding activity was examined in this example, by utilizing the glutathione-S-transferase (GST) fusion protein approach.

First, various GST fusion derivatives of MAD proteins were constructed containing deletions of either the N or C-terminal region of the protein. These GST fusion derivatives were then purified and their ability to bind radiolabeled enhancer regions of DPP regulated genes (quadrant enhancer region of vestigial gene, labial endoderm enhancer and ultrabithorax midgut enhancer) was analyzed by gel-shift assays.

The MAD binding site in these DPP responsive enhancer regions was delineated by using a DNaseI footprinting assay. As shown in FIG. 1a, MAD domain 1+linker, expressed as a GST fusion protein (designated MAD$^N$) bound DNA and protected a single interval within the quadrant enhancer, while GST and GST-MAD linker+domain 2 failed to bind DNA.

Figure 1B:
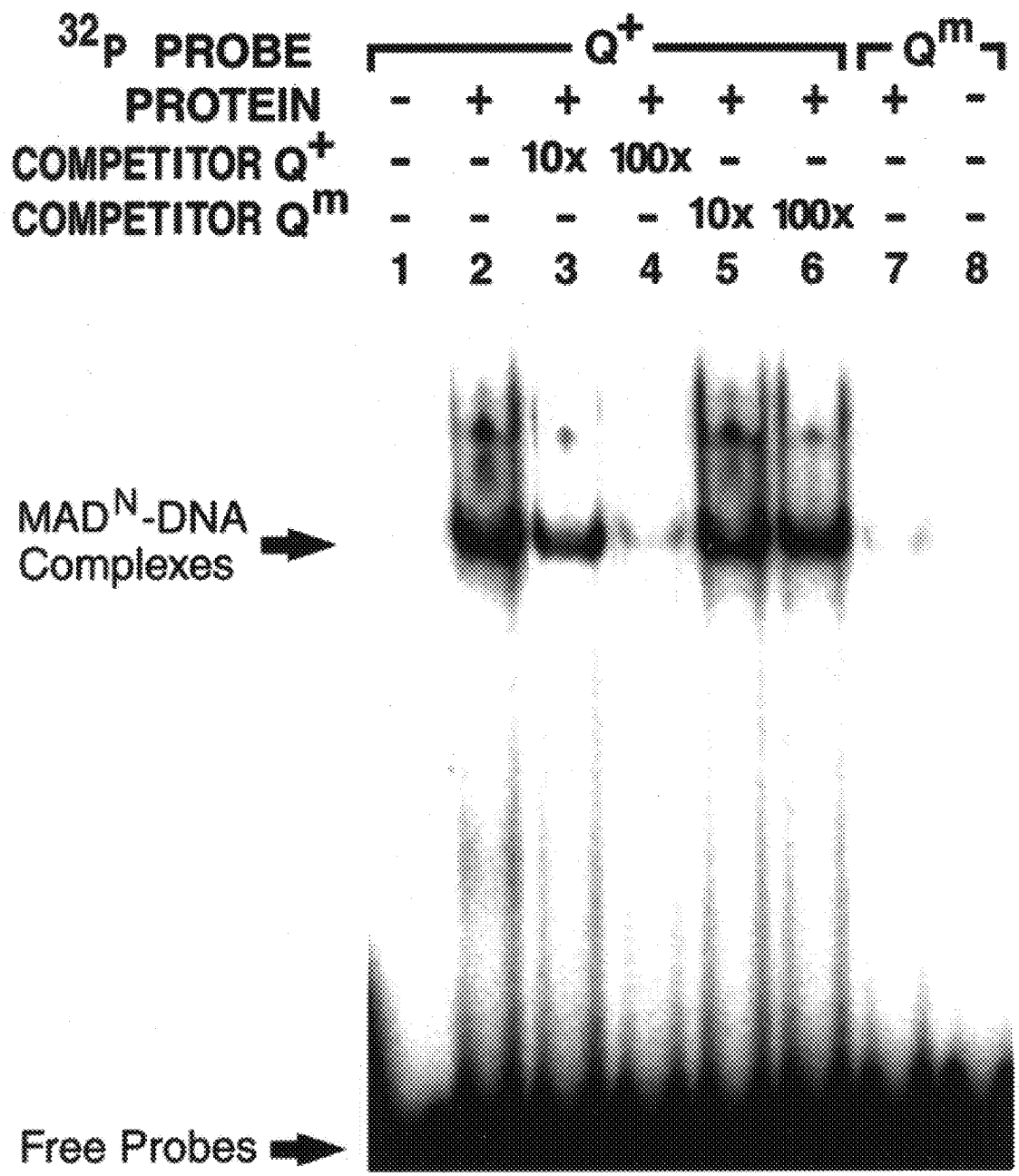
FIG. 1(b) is a photograph of an autoradiogram showing the results of a representative gel mobility shift competition assay used for assessing the binding specificity of MAD$^N$ to the vg quadrant enhancer DNA.

The specificity of MAD binding to these protected sequences was demonstrated by a gel mobility shift assay (see FIG. 1b). A 39 bp double-stranded oligonucleotide of the vg quadrant enhancer containing the MAD-protected region, the Q$^+$ probe, was bound readily by MAD$^N$ (FIG. 1b, lane 2) while a double-stranded oligonucleotide in which 12 bp of the MAD$^N$ protected region was replaced with two Bgl II restriction sites, the Q$^m$ probe, was bound with much lower affinity than the wild-type sequence (FIG. 1b, lane 7). Moreover, the Q$^m$ mutant oligonucleotide did not compete as efficiently as the Q$^+$ oligonucleotide with the $^{32}$P-labeled Q$^+$ probe (FIG. 1b, compare lanes 3 & 4 with lanes 5 & 6), indicating that binding of MAD$^N$ protein to the quadrant enhancer is specific. Only a single predominant band shift was observed regardless of competitor concentration (FIG. 1b, lanes 2–4) or probe sequence (FIG. 1b, lanes 2, 7, 8), indicating that MAD$^N$ binds to DNA as a single species.

Next, to determine whether the MAD$^N$ binding site is essential for the activation of the quadrant enhancer in vivo, transgenic fly lines were generated carrying a lacZ reporter gene under the control of the quadrant enhancer in which the 12 bp of the footprinted interval were replaced with one or two 6 bp Bgl II restriction sites, the 12 bp substitution corresponding in sequence to the Q$^m$ oligo that fails to bind Mad$^N$. Also, histochemical staining, indicated the quadrant enhancer is activated in early third instar discs as a small patch of expression near the intersection of the A/P and D/V boundaries and gradually fills in the entire wing pouch by the mid-late 3rd instar (Kim., J. et al, "Integration of positional signals and regulation of wing formation and identity by *Drosophila vestigial* gene, [*Nature* 382, 133–138, 1996). In contrast, expression of the lacz reporter gene driven by either mutated quadrant enhancer was not detectable in most early to mid 3rd instar discs. When detected, expression was observed at very low levels near the A/P boundary. These results, together with the in vitro data from the MAD binding experiments on the vg quadrant enhancer, demonstrate that MAD directly mediates the DPP-dependent transcription of the vg gene.

EXAMPLE 3

Figure 2A:
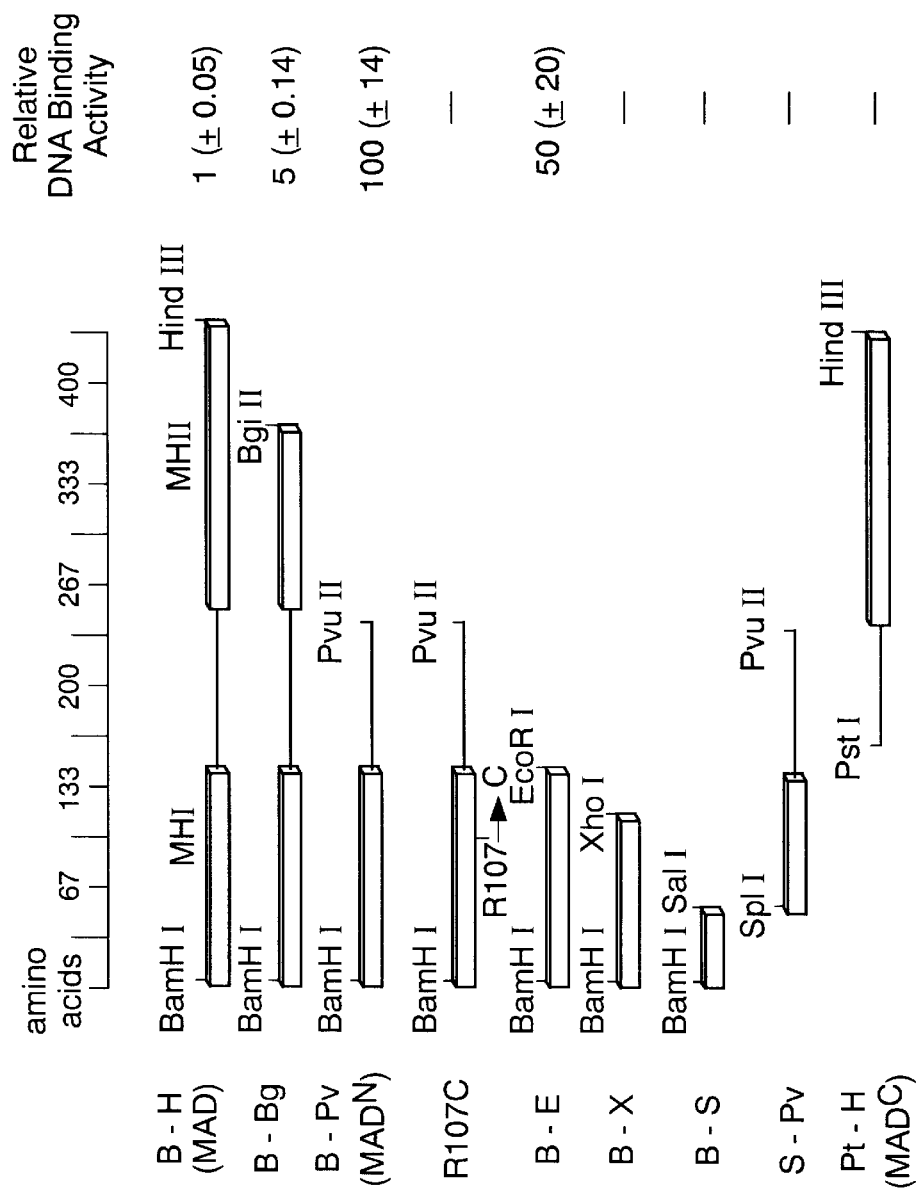
FIG. 2a) diagramatically shows the structure of MAD fusions to the carboxy-terminus of MBP/GST for use in DNA binding assays. Conserved domain 1 and domain 2 regions are shown as boxes, with the intervening linker region shown is indicated by a line. Fusion proteins contain the following MAD amino acids: B-H (MAD), 1–455; B-Bg, 1-372; B-Pv (MAD$^N$), 1-241; R107C, 1-241; B-E, 1-159; B-X, 1-120; B-S, 1-48; S-Pv, 49-241; Pt-H (MAD$^C$) 167–455. Amino acid residue number is indicated at the top of the panel. Relative DNA binding activity is shown at the right side. Protein concentrations were estimated by display on the SDS polyacrylamide gel shown in panel b. Data is from panel c and two additional repetitions of this experiment. Standard error is indicated within brackets.
Figure 2B:
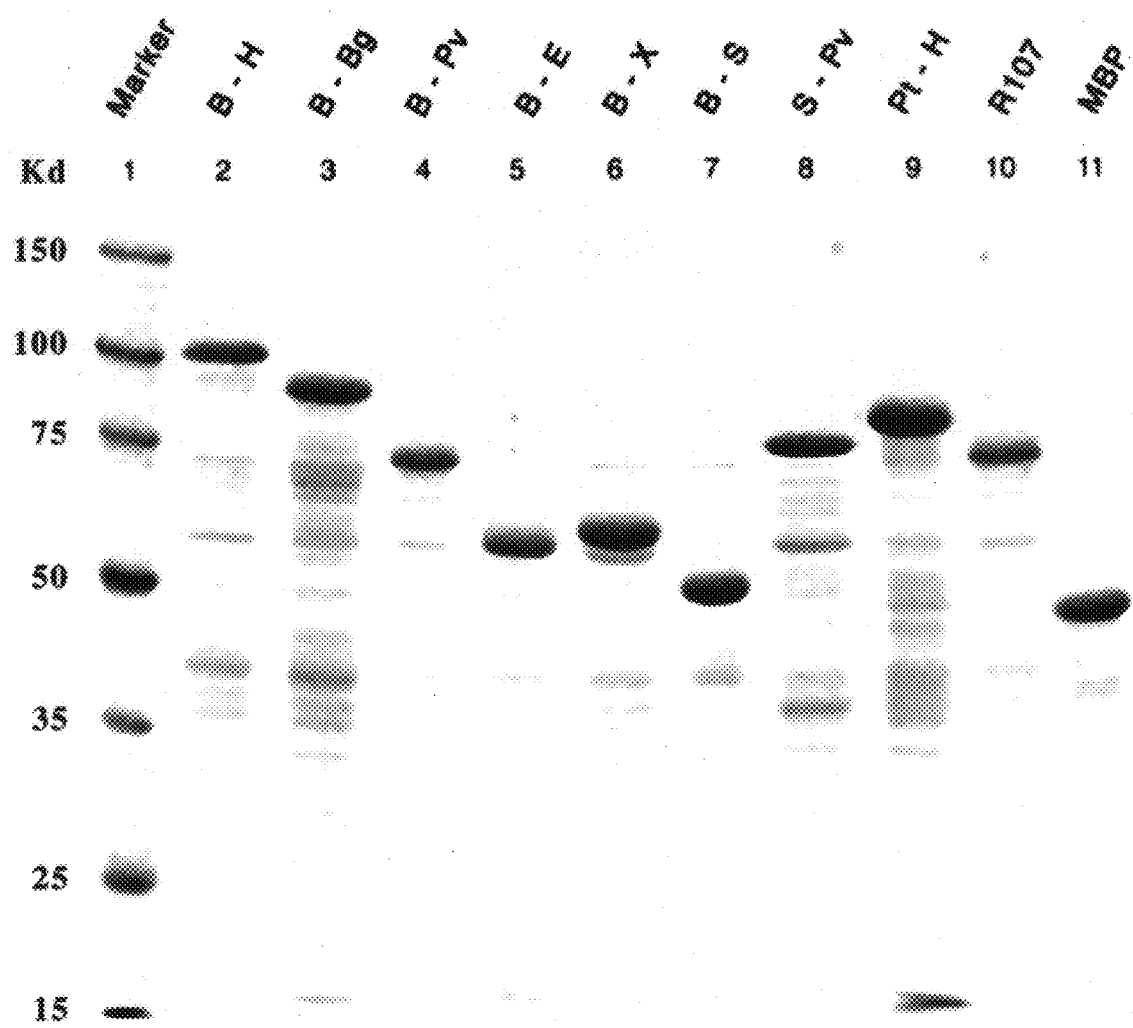
FIG. 2(b) is a photograph of a representative coomassie stained 10% SDS gel showing affinity purified preparations of MBP-fusion used in panel c. Size of markers (lane 1) is shown at left side.
Figure 2C:
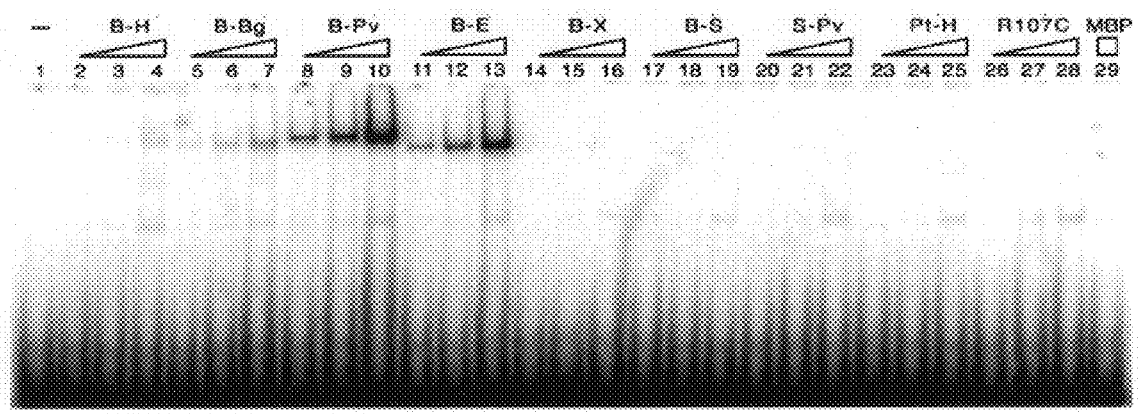

In this example, the N-terminal domain of MAD protein (MAD$^N$) is shown to bind to the vg quadrant enhancer. The identification of an essential MAD binding site in the quadrant enhancer in Example 2, enabled the precise localization of the MAD DNA binding domain in the following experiments. As depicted in FIG. 2a and b, in a series of fusions to E. coli maltose binding protein (MBP), the effects of deletions from the MAD carboxy and amino termini on DNA binding activity was tested using an oligonucleotide containing the MAD site of the quadrant enhancer (see FIG. 2c). The specific DNA-binding activity of full length MAD protein (B-H; lanes 2–4) was approximately 100-fold lower than that of C-terminally truncated MAD$^N$ (B-Pv; lanes 8–10), while removal of only a portion of domain 2 (B-Bg; lanes 5–7) resulted in intermediate activity. These results show that domain 2 effectively inhibits DNA binding and suggests a mechanism that might contribute to inactivation of MAD in the absence of DPP signaling. Removal of the linker region from the carboxy terminal end of domain 1 (B-E; lanes 11–13) caused a slight reduction in binding activity. Without domain 1, domain 2 plus linker region (MAD$^C$) failed to bind to DNA (Pt-H, lanes 23–25). Removal of the carboxy terminal (B-X; lanes 14–16) or amino terminal (S-PV 20–22) portion of the domain 1 abolished DNA binding activity. Binding also was abolished by a single amino acid substitution in MAD (Arg 107'Cys) that is the same as that found at position 133 in the Smad2 protein in a colorectal tumor (K. Eppert et al., "MADR2 Maps to 18q21 And Encodes A TGF beta-regulated MAD-related Protein That Is Functionally Mutated In Colorectal Carcinoma," Cell 86:543–552, 1996); (see R107C; lanes 26–28), demonstrating that this conserved residue is essential for domain 1 DNA binding activity. This example illustrates that the MAD-domain 1 region (MAD$^N$) harbors a sequence-specific DNA binding domain, and that this binding activity is inhibited in the full length MAD protein by the C-terminal domain 2 region (MAD$^C$).

EXAMPLE 4

In this example, lab endodermal and Ubx midgut enhancers are shown to contain MAD$^N$ binding sites similar to those in the vg quadrant enhancer. In the following set of experiments, the consensus sequence recognized by MAD$^N$ was determined. In addition to the vg quadrant enhancer, several other DPP-responsive enhancers, including the labial endoderm enhancer (Chouinard, S. & Kaufman, T. C., "Control of expression of the homeotic labial (lab) locus of Drosophila melanogaster: evidence for both positive and negative autogenous regulation," Development 13, 1267–1280, 1991; Tremml, G. & Bienz, M., "Induction of labial expression in the Drosophila endoderm: response elements for dpp signalling and for autoregulation," Development 116, 447–456, 1992), and the Ultrabithorax midgut enhancer, the DPP response element has been localized to the 95 bp DI-DII interval (Thuringer, F., et al, "Dissection of an indirect autoregulatory response of a homeotic Drosophila gene," EMBO J. 12, 2419–2430, 1993). Gel shifts with oligonucleotides representing portions of these enhancers (FIG. 3b; lanes 1–18), and the competition of Q$^+$ but not Q$^m$ for these oligonucleotides (FIG. 3b; lanes 9–12, 15–18), reveal that at least one high affinity MAD$^N$ binding site is found in each, along with multiple low affinity sites. Alignment of these sequences (SEQ ID NO:4); (SEQ ID NO:5); (SEQ ID NO:6); (SEQ ID NO:7); (SEQ ID NO:8) and comparison of the relative strength of MAD$^N$ binding were used to derive a MAD$^N$ binding site consensus of (SEQ ID NO:9) GCCGnCGC. The two highest affinity sites matched this consensus perfectly while three lower affinity sites contained mismatches at one to three positions (FIG. 3c).

The results presented in this example demonstrate that MAD domain 1 region harbors a sequence-specific DNA binding domain, and indicate that this DNA-binding activity plays an important role in directing transcriptional activation in response to DPP signaling. The C-terminal domain 2 region, in addition to its previously demonstrated function as a transcriptional activation domain (in the case of Smad 1, see F. Liu et al., "A Human Mad Protein Acting As A BMP-regulated Transcriptional Activator," Nature 381:622–623, 1996), inhibits DNA binding activity of domain 1 in vitro. This example identifies an important mechanism by which the Mad gene product activates expression of DPP regulated genes, a crucial step in the TGF-β signal transduction pathway.

EXAMPLE 5

Figure 4:
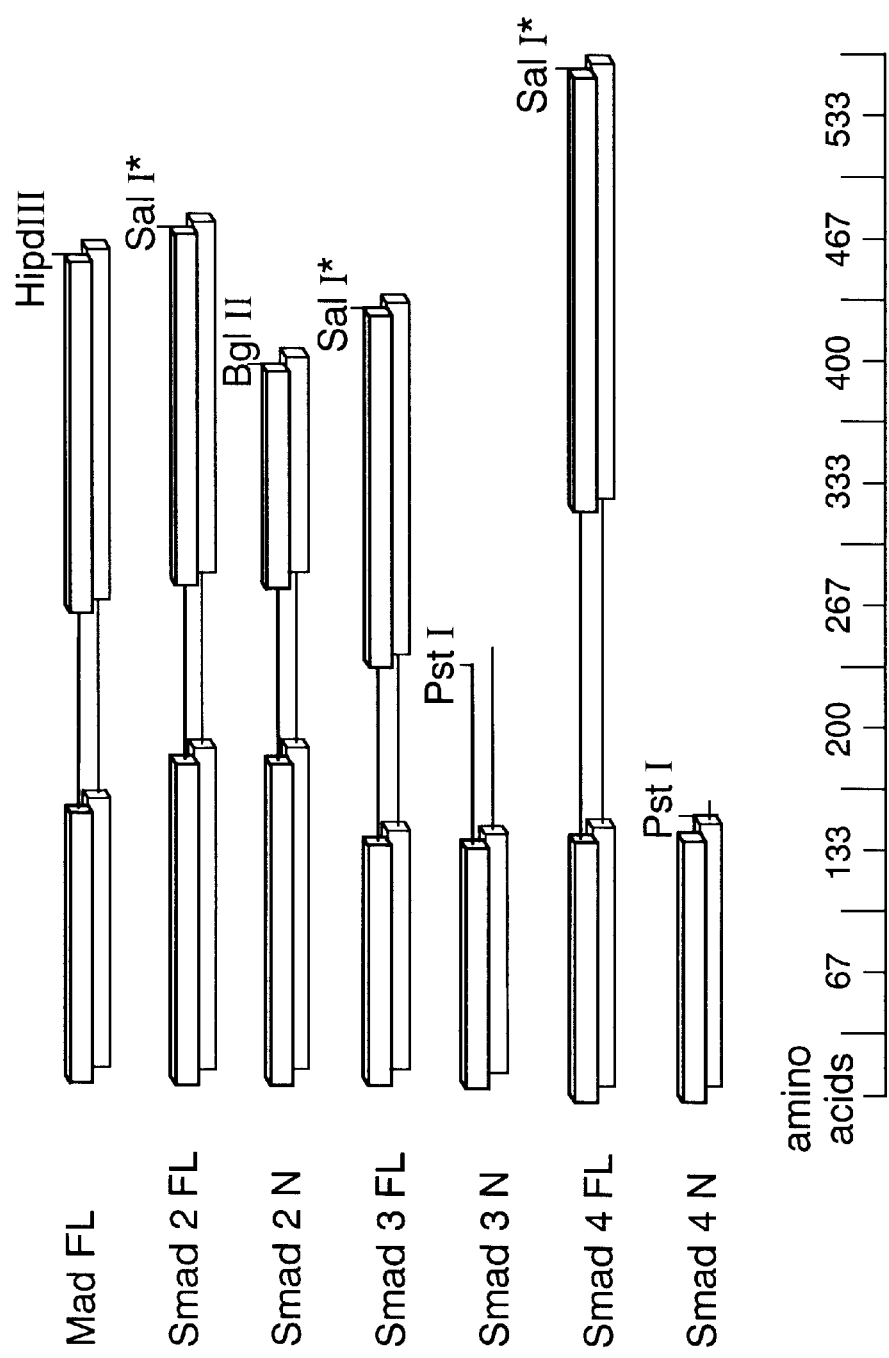
FIG. 4 diagramatically shows the structure of Smad fusions to the carboxy-terminus of E.coli maltose binding protein (MBP{New England Biolabs}) for use in DNA binding assays. Shaded boxes indicate conserved Smad domains 1(left) and 2(right) regions, separated in each case by a relatively non-conserved linker region indicated by a line. Maltose binding protein is not shown. Fusions are either full-length (FL) or C-terminally truncated (N) Smads. Relevant restriction endonuclease cleavage sites are as shown. Length of the protein is indicated by the scale denoting the amino acid residue number at the bottom of the panel.
Figure 6A:
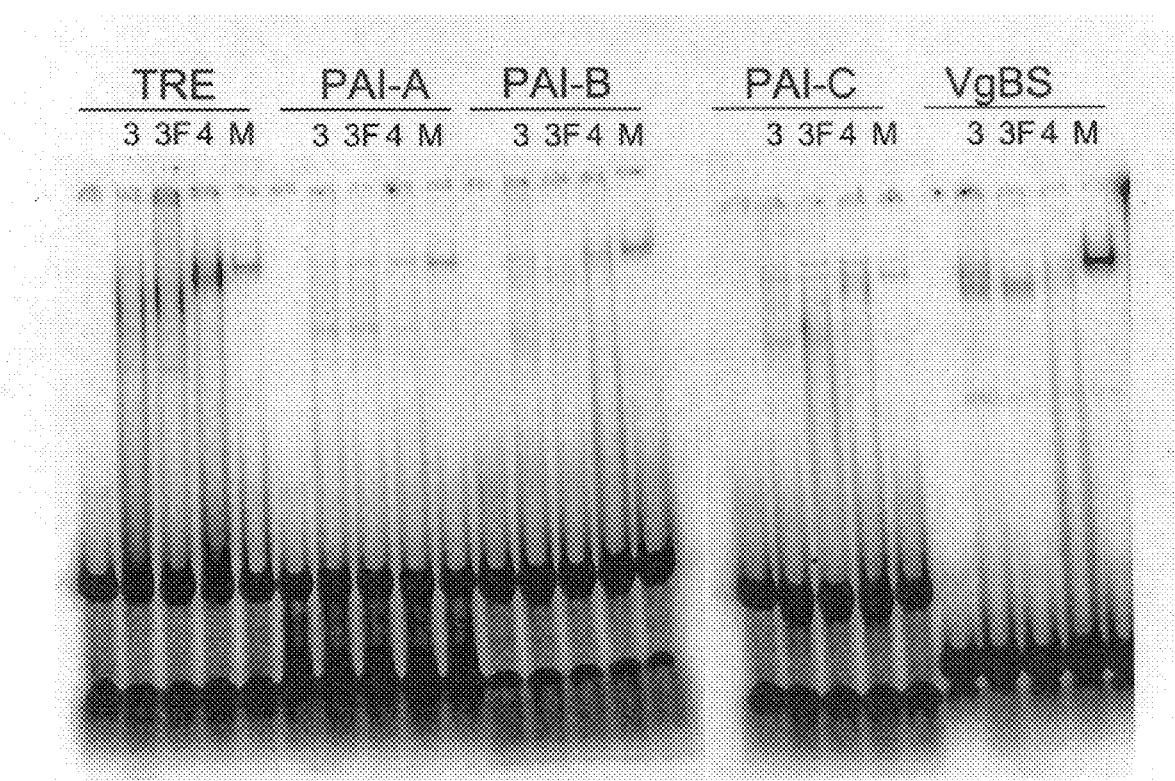
FIG. 6A shows full length Smad3 and Smad4 proteins bind preferentially to the human collagenase TRE element. Shown is a photograph of an autoradiogram showing the results of a representative gel mobility shift assay used for assessing the ability of MBP-Smad fusions to bind to $^{32}$P-end-labeled TRE, PAI-A, PAI-B, PAI-C DNA oligonucleotide probes as denoted in FIG. 5, VgBS: oligonucleotide probe as denoted in FIG. 3c. For each probe, Lane 1: no protein control, Lane 2:3, MBP-Smad3N; Lane 3: 3F, MBP-Smad3FL; Lane 4:4, MBP-Smad4FL; Lane 5: M, MBP-MADN.
Figure 6B:
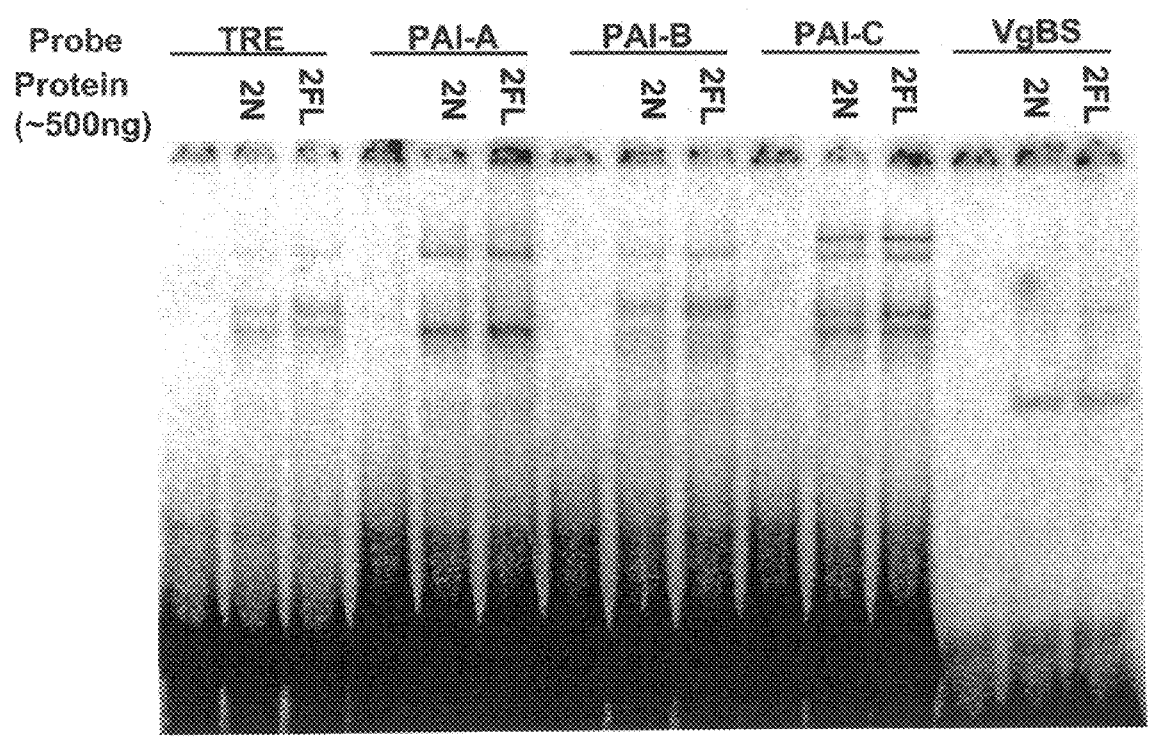
FIG. 6B shows full length Smad2 binds preferentially to two intervals within the PAI-TGF-β response element. Shown is a photograph of an autoradiogram which indicates the results of a representative gel mobility shift assay, assessing the ability of MBP-Smad fusions to bind to $^{32}$P-end-labeled TRE, PAI-A, PAI-B, PAI-C DNA oligonucleotide probes as denoted in FIG. 5, VgBS: oligonucleotide probe as denoted in FIG. 3. For each probe, Lane 1: no protein control, Lane 2:2N, MBP-Smad2N; Lane 3:2FL, MBP-Smad2FL.
Figure 6C:
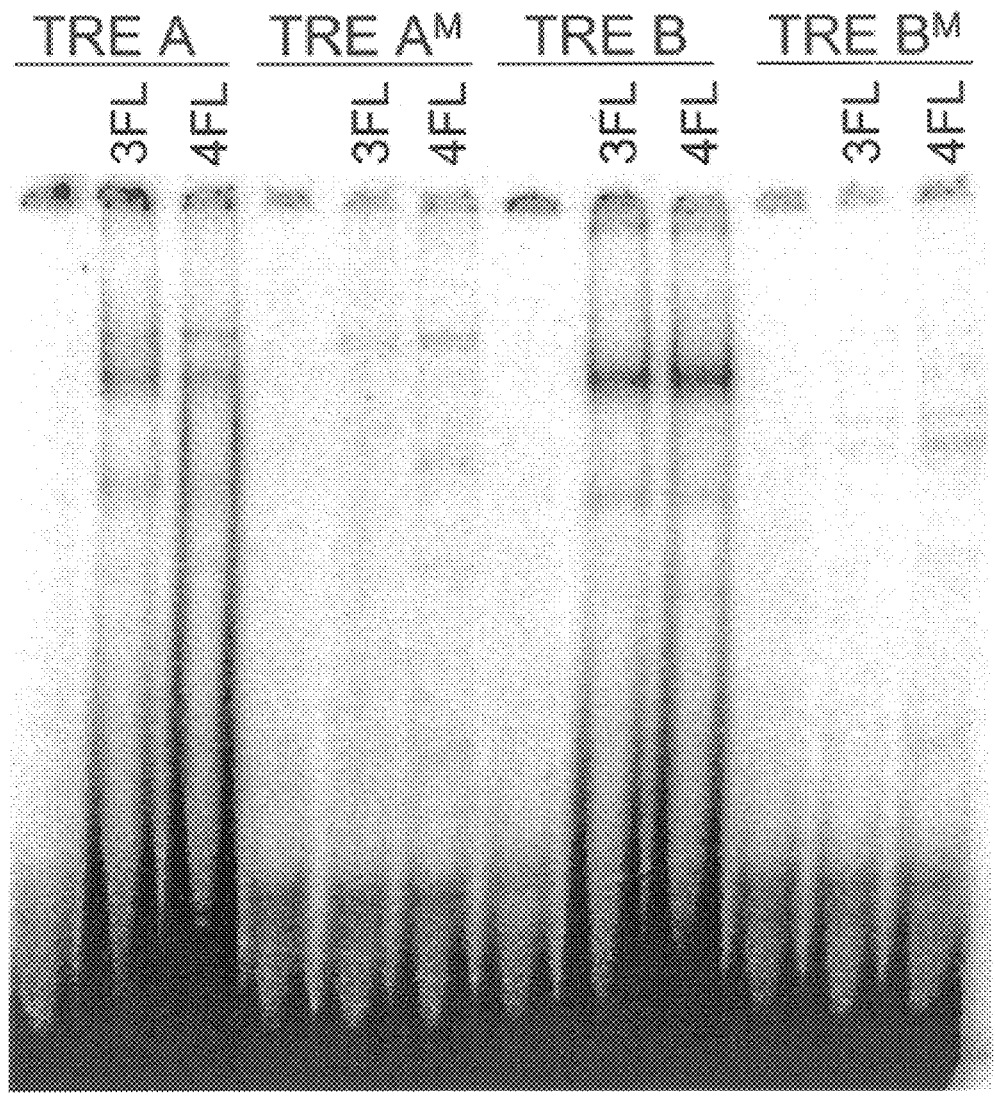
FIG. 6C shows Mutations in GNC triplets disrupt binding by Smad3 and Smad4. Shown is a photograph of an autoradiogram indicating the results of a representative gel mobility shift assay, assessing the ability of MBP-Smad fusions to bind to $^{32}$P-end-labeled wild-type TREA, and TREAB and its mutant derivatives, TREA$^M$ and TREB$^M$ DNA oligonucleotide probes as denoted in FIG. 5. For each probe, Lane 1: no protein control, Lane 2:3FL, MBP-Smad3FL; Lane 3:4FL, MBP-Smad4FL.
Figure 6D:
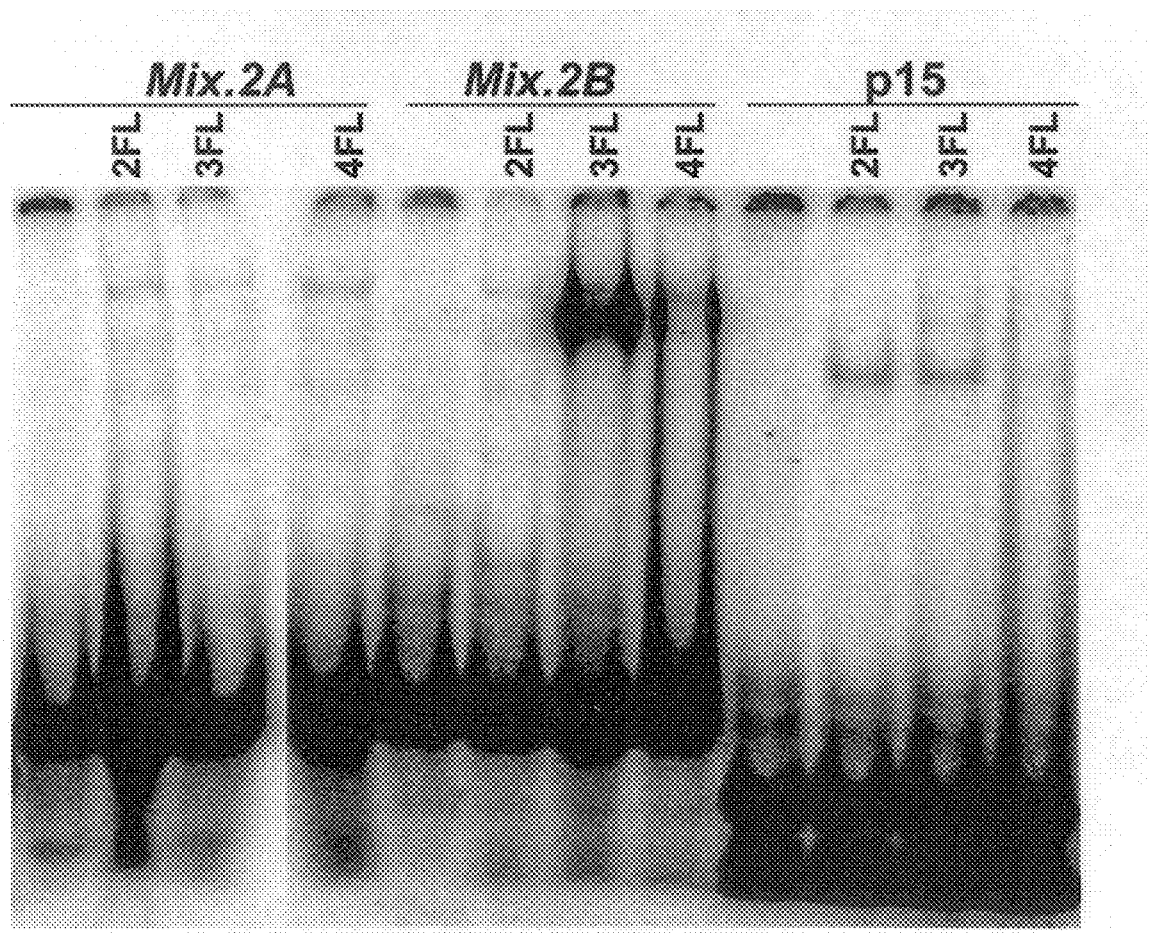
FIG. 6D shows Smad2, Smad3 and Smad4 exhibit distinct DNA-binding specificities. Shown is a photograph of an autoradiogram indicating the results of a representative gel mobility shift assay, assessing the ability of MBP-Smad fusions to bind to $^{32}$P-end-labeled wild-type Mix.2A, Mix.2B and p15 DNA oligonucleotide probes as denoted in FIG. 6. For each probe, Lane 1: no protein control, Lane2:2FL, MBP-Smad2FL; Lane3:3FL, MBP-Smad3FL; Lane:4FL, MBP-Smad4FL.

In this example, MAD and related Smad polypeptides are shown to have similar but distinct DNA binding specificities. In the first set of experiments, Smad-or MAD-DNA binding activity was examined utilizing the maltose binding protein(MBP)-fusion approach. First, various MBP fusion derivatives of MAD, Smad2, Smad3 and Smad4 proteins were constructed containing either full length or C-terminally truncated regions of the protein (see FIG. 4). These MBP fusion derivatives were then purified and their ability to bind various radiolabeled TGF-β response element oligonucleotide probes was analyzed by gel-shift assays. FIG. 5 shows the sequences (SEQ ID NO:10); (SEQ ID NO:11); (SEQ ID NO:12); (SEQ ID NO:13); (SEQ ID NO:14); (SEQ ID NO:15) of the wild-type and mutant TGF-β response element oligonucleotide probes used for the assays; Drosophila vestigial quadrant enhancer(20 bp) containing the MAD binding site, −74 to −42 TPA response element (TPA) of the human collagenase gene, PAI-A, -B, -C: overlapping oligonucleotides of the plasminogen activator inhibitor gene, Mix.2: Activin-responsive element (ARE) of the Xenopus Mix.2 gene, p15: oligonucleotide probe that spans −83 to −66 TGF-β response element of the human p15$^{INK4B}$ gene. The results of the gel-shift analysis are shown in FIG. 6. Full-length Smad3 and Smad4 preferentially binds the human collagenase TRE element (FIG. 6a), whereas full-length Smad2 preferentially binds to two intervals; PAI-A and PAI-C within the PAI-TGF-β response element(FIG. 6b). Further, mutations in the GNC triplets in the TPA response element (TPA) of the human collagenase gene, TREA$^M$ and TREB$^M$ disrupts binding by Smad3 and Smad4 (FIG. 6c). Also, Smad2, Smad3 and Smad4 exhibit distinct DNA binding specificities to Mix.2A, Mix.2B and p15 oligonucleotide probes (see FIG. 6d).

Figure 7A:
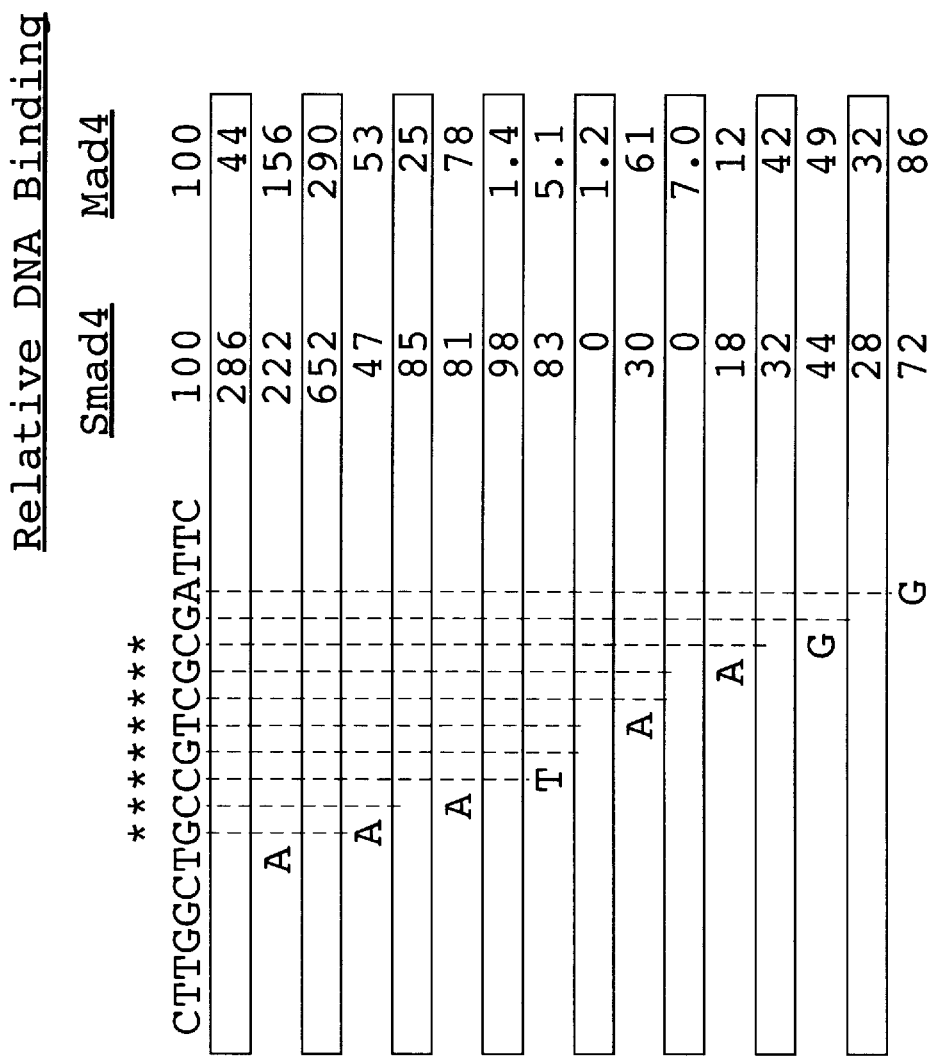
FIG. 7A shows MAD and Smad4 have similar but distinct DNA-binding specificities as revealed by mutational analysis. The nucleotide sequence (SEQ ID NO:8) at the top indicates the double-stranded(ds) wild-type 20 bp oligonucleotide containing the vg quandrant enhancer MAD binding site. The region that shows significant homology with the lab(endodermal enhancer) and Ubx(midgut enhancer) MAD binding site (see aligned sequence (SEQ ID NO:9) in FIG. 3c) is indicated. The relative binding affinities of the MADN-MBP and the Smad4FL-MBP fusion proteins for the mutant 20 bp oligonucleotide probe are expressed relative to the wild-type probe, as the ratios of bound to free ds probes in gel-shift assays.

In the next set of experiments, by mutational analysis, the relative binding specificities of MAD and the Smad4 protein to bind wild-type and various mutant derivatives (having single nucleotide substitutions) of the vg quadrant enhancer MAD binding site was compared. Mad and Smad4 binding affinities were quantitated by imaging the band shift gels using a Molecular Dynamics Phosphor Imager. Relative affinities were calculated as the ratio of bound probe to free probe at a particular protein concentration. Protein concentrations were estimated from the intensity of bands on Coomassie Brilliant Blue-stained SDS polyacrylamide gels. All experiments were done using MBP fusion proteins purified from E. coli extracts by amylose affinity chromatography. Results shown are an average mean of three experiments. As diagrammatically shown in FIG. 7a, depending on the single nucleotide substitutions in the homologous TGF-β response element region (*) in the vg quadrant enhancer binding site, Smad4- and Mad-DNA binding is affected to different degrees. For some single nucleotide substitutions, DNA binding by both Smad4 and Mad polypeptides is totally abolished or diminished to a similar degree, whereas for other substitutions, either Smad- or Mad-DNA binding is affected.

In conjunction with the above experiments, mutational analysis also revealed that specific nucleotide substitutions at particular positions in the cognate binding site (see FIG. 7b (SEQ ID NO:16); (SEQ ID NO:17) downward arrow and *) renders the site with 6×higher affinity for the MAD polypeptide.

In total, these experiments indicate Mad and Smads have similar but distinct DNA binding specificities, and certain mutations in the binding site actually provides for better binding.

EXAMPLE 6

Figure 7C:
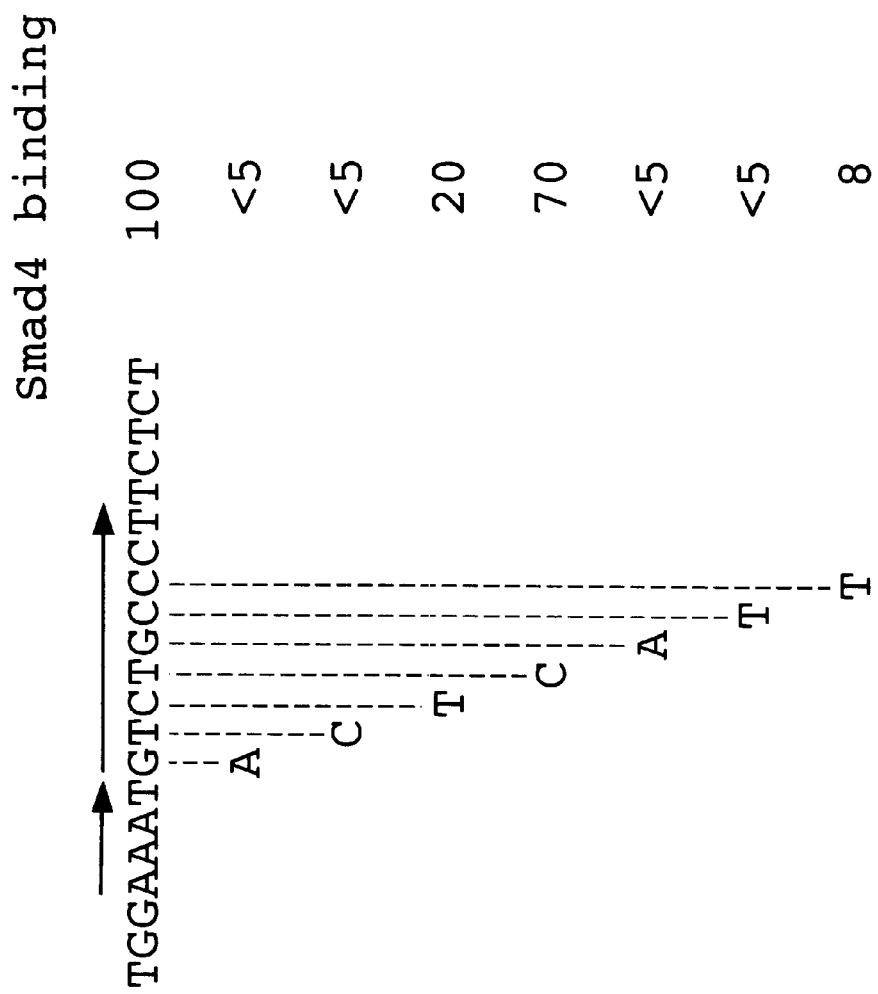
FIG. 7C shows that Smad4 binding for a portion of the sequence (SEQ ID NO:18) of the Mix.2 gene is affected by single base changes.

In this Example, Smad 4 binding was assessed on a portion of the sequence (SEQ ID NO:18) of the Mix.2 gene [See *Nature* 383:691–696 (1996)] in the manner as described above. The relative binding affinity is affected by single base changes (FIG. 7c).

From the above examples, it should be clear that the present invention contemplates DNA binding of MAD and Smad proteins. The binding results in peptide-nucleic acid binding complexes. In one embodiment, the complexes comprise at least a portion of a purified Smad polypeptide specifically bound to DNA. In another embodiment, the Smad polypeptide is a fragment of the naturally-occurring polypeptide. The present invention contemplates the situation where either i) the polypeptide is bound non-covalently to a region of the DNA comprising a wild-type sequence, or the polypeptide is bound non-covalently to a region of the DNA comprising a mutant sequence.

We claim:

1. A composition comprising a peptide-nucleic acid binding complex comprising at least a portion of a purified MAD polypeptide specifically bound to DNA.

* * * * *